(12) United States Patent
Boyette

(10) Patent No.: US 9,101,791 B2
(45) Date of Patent: Aug. 11, 2015

(54) SYSTEMS AND METHODS FOR OPTIMIZING MUSCLE DEVELOPMENT

(71) Applicant: Robert B. Boyette, Wall Township, NJ (US)

(72) Inventor: Robert B. Boyette, Wall Township, NJ (US)

(*) Notice: Subject to any disclaimer, the term of this patent is extended or adjusted under 35 U.S.C. 154(b) by 0 days.

(21) Appl. No.: 14/554,640

(22) Filed: Nov. 26, 2014

(65) Prior Publication Data

US 2015/0080184 A1 Mar. 19, 2015

Related U.S. Application Data

(63) Continuation of application No. 14/450,785, filed on Aug. 4, 2014, now Pat. No. 8,900,099.

(60) Provisional application No. 61/862,159, filed on Aug. 5, 2013.

(51) Int. Cl.
*A63B 24/00* (2006.01)

(52) U.S. Cl.
CPC ............. *A63B 24/0075* (2013.01); *A63B 24/00* (2013.01)

(58) Field of Classification Search
CPC ............................ A63B 24/00; A63B 24/0075
USPC .......................................... 482/1–9, 900–902
IPC ........................................................ A63B 24/00
See application file for complete search history.

(56) References Cited

U.S. PATENT DOCUMENTS

| | | | | | |
|---|---|---|---|---|---|
| 4,828,257 | A | * | 5/1989 | Dyer et al. | 482/5 |
| 4,865,315 | A | * | 9/1989 | Paterson et al. | 482/5 |
| 4,934,694 | A | * | 6/1990 | McIntosh | 482/9 |
| 8,287,434 | B2 | * | 10/2012 | Zavadsky et al. | 482/5 |
| 8,574,130 | B1 | * | 11/2013 | Stearns et al. | 482/8 |
| 8,900,097 | B1 | * | 12/2014 | Griggs et al. | 482/4 |
| 2010/0216600 | A1 | * | 8/2010 | Noffsinger et al. | 482/5 |
| 2014/0287876 | A1 | * | 9/2014 | Etter et al. | 482/5 |

* cited by examiner

*Primary Examiner* — Glenn Richman
(74) *Attorney, Agent, or Firm* — Lowenstein Sandler LLP

(57) ABSTRACT

Systems and methods for optimizing muscle development are disclosed. A method includes identifying one or more parameters of a user and force data associated with the user. The force data corresponds to an exercise to be performed by the user. The method further includes generating an exercise program to be executed using an exercise device, and determining a resistance to be applied by the exercise device during execution of the exercise program. The resistance is determined based at least partially on the force data and the one or more parameters of the user.

10 Claims, 12 Drawing Sheets

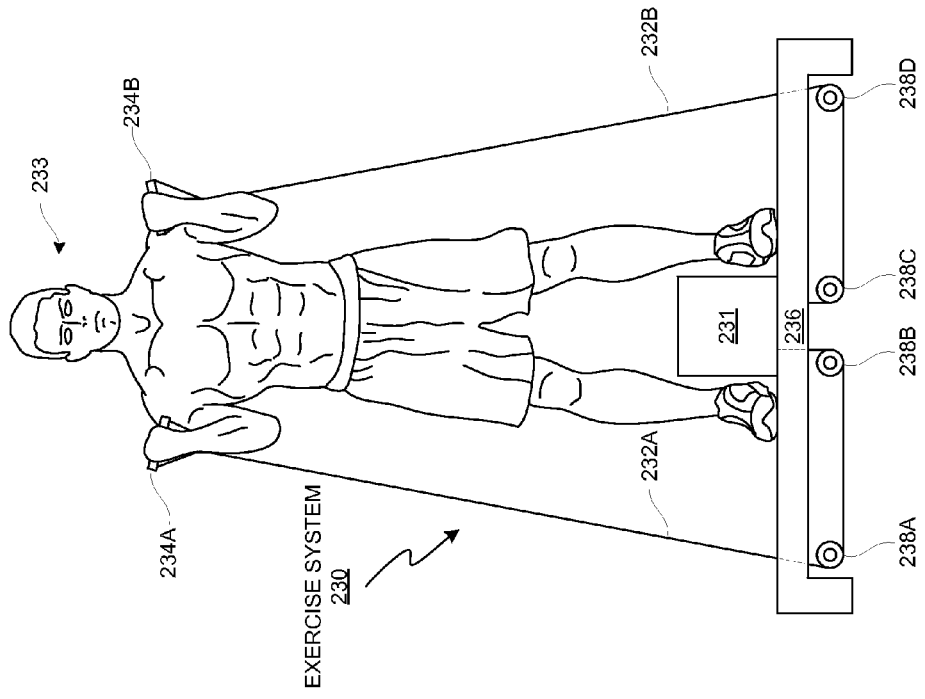
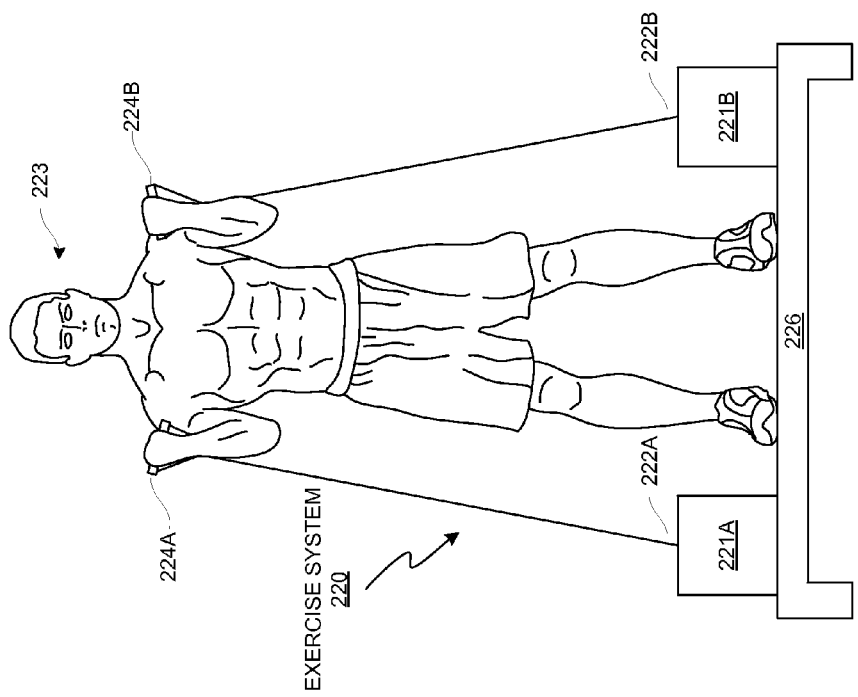

SYSTEMS AND METHODS FOR OPTIMIZING MUSCLE DEVELOPMENT

CROSS-REFERENCE TO RELATED APPLICATION

This application is a continuation of U.S. patent application Ser. No. 14/450,785, filed Aug. 4, 2014, which claims the benefit of priority of U.S. Provisional Application No. 61/862,159, filed Aug. 5, 2013, both of which are hereby incorporated by reference herein in their entireties.

TECHNICAL FIELD

This disclosure relates to the field of exercise devices, in particular, to exercise devices and systems designed to optimize muscle development.

BACKGROUND

Exercise equipment is often designed to provide a user with pre-defined exercise plans that may adapt to the user's performance. However, such equipment often focuses on increasing cardiovascular endurance but fails to optimize muscle development by not taking into account maximum exertion levels of the user as well as muscle recovery time. Moreover, such equipment can be difficult to set up and expensive, and does not provide the goal-driven direction that the user may receive from working with a personal trainer.

BRIEF DESCRIPTION OF THE DRAWINGS

The present disclosure is illustrated by way of example, and not by way of limitation, in the figures of the accompanying drawings, in which:

FIG. 2B illustrates an exercise system according to an implementation of the disclosure;

FIG. 2C illustrates an exercise system according to another implementation of the disclosure;

DETAILED DESCRIPTION

Figure 1:
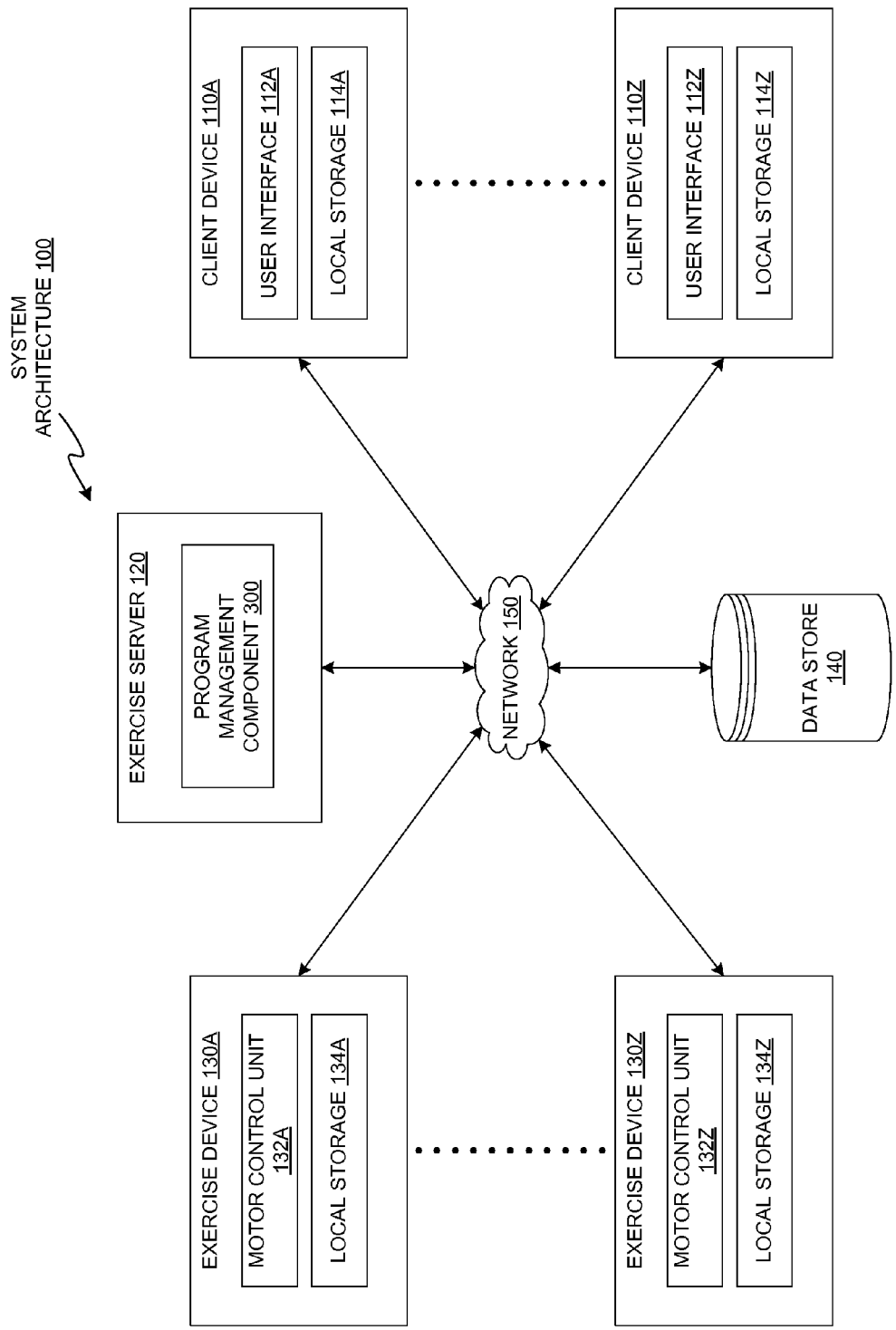
FIG. 1 illustrates an example system architecture in accordance with an implementation of the disclosure.

Described herein are systems and methods for optimizing muscle development. The described implementations may facilitate the development of an optimized exercise program for a specific user. An exercise system, as described herein, may play the role of a personal trainer to guide the user through the optimized exercise program and maintain a record of his/her performance. Moreover, the exercise system may combine motorized exercise equipment with a portable device of the user, such as a smart phone, providing a personalized and user-friendly interface.

Unlike traditional exercise equipment, the implementations described herein may be performed without training and with minimal setup on the part of the user. When the user starts out, and if the user is a new user, the system may request biographical parameters, such as name, age, weight, and sex. The user may then be asked to specify his/her goal (e.g., to get stronger, to stay in shape, etc.), and how much time the user is willing to spend achieving that goal. The user may also be asked to provide user-proposed times for when he/she would prefer to exercise. Based on these parameters, the system may automatically calculate the optimal training program for that specific user. The system may generate a schedule of workout sessions, including which specific exercises to perform, on which dates/times the exercises are to be performed, how many sets and repetitions per set to perform, etc. The system may then initialize the first exercise, ask the user to perform one repetition to his/her maximum ability (e.g., to measure the user's one-rep maximum), and based on the one-rep maximum, as well as biographical data and the user's goals, set the appropriate resistance for the user. The user may then be instructed to perform a number of repetitions at these settings. When the exercise is completed, the system may repeat the calibration process to setup for the next muscle group until the exercise session is completed, or may initialize all exercises prior to instructing the user to performing the repetitions of each of the exercises.

In one aspect, a method includes identifying a plurality of parameters of a user and generating an exercise program based at least partially on the plurality of parameters. The exercise program includes a plurality of exercises, and for each of the plurality of exercises, the method further includes identifying one-rep maximum data associated with the exercise, in which the one-rep maximum data was captured by the exercise device during operation by the user. The method further includes, for each of the plurality of exercises, determining, for the exercise, a resistance to be applied by the exercise device during execution of the exercise program, in which the resistance is determined based at least partially on the one-rep maximum data associated with the exercise.

In another aspect, a method includes generating for display, by a client device, a first indication to a user instructing the user to start performing an exercise using an exercise device, in which the exercise device includes a handle located at a first position. The method further includes, in response to detecting displacement of the handle from the first position, causing the exercise device to maintain a first pre-defined speed of the handle as the handle is displaced from the first position to a second position. The method further includes detecting that the handle is located at the second position. The method further includes generating for display, by the client device, a second indication to the user instructing the user to displace the handle to the first position. The method further includes, in response to detecting displacement of the handle from the second position, causing the exercise device to maintain a second pre-defined speed of the handle as the handle is displaced from the second position to the first position.

In another aspect, an exercise device includes a housing. The housing includes a motor, a motor control unit operatively coupled to the motor, a spool operatively coupled to the motor, and a tension gauge communicatively coupled to the motor control unit. The exercise device further includes a tension line having a first end and a second end, in which the first end is connected to the spool, and at least a portion of the tension line is contained within the housing. The tension gauge may be configured to measure at least one of a force applied to the tension line or a rotational velocity of the spool. The exercise device further includes a handle connected to the second end of the tension line.

In one or more of the disclosed implementations, systems (e.g., systems including memories, processing devices, etc.) for performing operations of the aforementioned methods are also disclosed. Additionally, in implementations of the disclosure, a computer-readable storage medium (e.g., a non-transitory computer-readable storage medium) may store methods for performing the operations of the aforementioned methods.

FIG. 1 illustrates an example system architecture 100, in accordance with an implementation of the disclosure. The system architecture 100 includes client devices 110A-110Z, an exercise server 120, exercise devices 130A-130Z, a data store 140, and a network 150.

In one implementation, the client devices 110A-110Z may each include computing devices such as personal computers (PCs), laptops, mobile phones, smart phones, tablet computers, netbook computers etc. Client devices 110A-110Z may also be referred to as "user devices". An individual user may be associated with (e.g., own and/or use) one or more client devices (e.g., one or more of client devices 110A-110Z). Client devices 110A-110Z may each be owned and utilized by different users at different locations. As used herein, a "user" may refer generally to an individual operator of one or more of client devices 110A-110Z and/or one or more of exercise devices 130A-130Z.

The client devices 110A-110Z may each implement user interfaces 112A-112Z, respectively. Each of user interfaces 112A-112Z may allow a user of the respective client device 110A-110Z to send/receive information to/from the exercise server 120 and any of exercise devices 130A-130Z. For example, one or more of the user interfaces 112A-112Z may be a web browser interface that can access, retrieve, present, and/or navigate content (e.g., web pages such as Hyper Text Markup Language (HTML) pages) provided by the exercise server 120. In one implementation, one or more of the user interfaces 112A-112Z may be a standalone application (e.g., a mobile app), which may have been provided by the exercise server 120 (e.g., as a downloadable application), that allows a user of a respective client device 110A-110Z to send and receive information to the exercise server 120. In one implementation, the user interfaces 112A-112Z guide their respective users in performing personalized exercise programs. Each of the client devices 110A-110Z may include local storages 114A-114Z, respectively, for storing user interface data, exercise program data, exercise history, user preference information, etc. In some implementations, some or all of the data stored in one or more of the local storages 114A-114Z may be synchronized with the exercise server 120.

In one implementation, the exercise server 120 may be one or more computing devices (such as a rackmount server, a router computer, a server computer, a personal computer, a mainframe computer, a laptop computer, a tablet computer, a desktop computer, etc.), data stores (e.g., hard disks, memories, databases), networks, software components, and/or hardware components. The exercise server 120 may include a program management component 300 (which may be executed by a processing device of the exercise server 120) that is capable of generating an exercise program for a user, updating the exercise program, synchronizing exercise program data between one or more devices, and interfacing with one or more of exercise devices 130A-130Z (e.g., controlling and receiving feedback from one or more of exercise devices 130A-130Z). In some implementations, the program management component 300 may be implemented on a different device than exercise server 120. For example, in some implementations, one or more of the client devices 110A-110Z may implement the program management component 300 (or at least some of the functionality of the program management component 300). In some implementations, one or more of the exercise devices 130A-130Z may implement the program management component 300 (or at least some of the functionality of the program management component 300). In some implementations, some or all of the functionality of the program management component 300 may be distributed across one or more of the client devices 110A-110Z and one or more of the exercise devices 130A-130Z. In some implementations, the exercise server may be omitted from the system architecture 100.

In one implementation, the exercise server 120 may maintain records of one or more users' activities with respect to one or more of the client devices 110A-110Z and/or one or more of the exercise devices 130A-130Z. For example, the exercise server may be an exercise server 120 operated and/or maintained by a doctor, therapist (e.g., a physical therapist), insurance provider, exercise facility, etc. that allows for monitoring of the activity/progress of one or more users of the exercise devices 130A-130Z. As an example, a physical therapist may monitor the progress of a user (e.g., a patient recovering from injury) of the exercise device 130A to track the progress and/or recovery of the user over time, while updating the exercise program periodically to adapt to the user's progress. As another example, an insurance provider may provide a discount to a user of the exercise device 130A provided that monitored activity of the user satisfies a threshold activity requirement (e.g., that the user successfully performs one or more periodically scheduled exercises with the exercise device 130A). In some implementations, users may share their progress and results with others by transmitting their associated exercise history data to a social media service.

In one implementation, the exercise devices 130A-130Z may be used by one or more users to perform a variety of different exercises. The users may be the same as or different from the users of the client devices 110A-110Z. As an example, a user of the exercise device 130A may also be a user of the client device 110A. As another example, a user of the exercise device 130A may be different than a user of the client device 110A. As another example, a user may operate the exercise device 130A while simultaneously operating the client device 110A. As another example, a user may operate one or more of the exercise devices 130A-130Z without operating any of client devices 110A-110Z. As another example, a user may operate one or more of the client devices 110A-110Z without operating any of the exercise devices 130A-130Z. As another example, a first user may operate the exercise device 130A while a second user operates the client device 110A (e.g., the second user supervises the first user). As another example, a first user may operate two or more of the exercise devices 130A-130Z while simultaneously operating client device 110A. The foregoing examples are meant for illustrative purposes, as any number of users may use/operate any of the client devices 110A-110Z and the exercise devices 130A-130Z in accordance with the implementations described herein, as would be appreciated by one of ordinary skill in the art. Moreover, the client devices 110A-110Z do not necessarily map to the exercise devices 130A-130Z, respectively. For example, the client device 110B may send/receive information to/from the exercise device 130A.

In one implementation, each of the exercise devices 130A-130Z includes motor control units 132A-132Z, respectively. In one implementation, one or more of the motor control units 132A-132Z includes a microprocessor (e.g., a complex instruction set computing (CISC) microprocessor, a reduced instruction set computing (RISC) microprocessor, a very long instruction word (VLIW) microprocessor, a processor implementing other instruction sets, or processors implementing a combination of instruction sets) and/or a special-purpose processing device (e.g., an application specific integrated circuit (ASIC), a field programmable gate array (FPGA), a digital signal processor (DSP), or a network processor). In one implementation, one or more of the motor control units 132A-132Z includes a network interface for communicating with other devices (e.g., via the network 105).

The motor control units 132A-132Z may control an amount of resistance experienced by a user of a respective exercise device, a relative location of an exercise device component (e.g., a handle), a speed of the exercise device component (e.g., a rate at which a handle is or can be moved), etc. In one implementation, one or more of the motor control units 132A-132Z may be controlled by one or more of the client devices 110A-110Z. For example, the client device 110A may transmit an instruction (e.g., via the network 150) to the exercise device 130A, which may cause the motor control unit 132A to rotate or lock a motor of the exercise device 130A. In one implementation, one or more of the motor control units 132A-132Z may transmit information to one or more of the client devices 110A-110Z. For example, the motor control unit 132A may transmit (e.g., via the network 150) data indicative of a force applied to a component of the exercise device 130A (e.g., force applied to a handle by a user), a relative position of the component, a speed of the component (e.g., a speed at which a handle is being pushed or pulled by the user), etc. In one implementation, one or more of client devices 110A-110Z may be combined with one or more of exercise devices 130A-130Z. In one implementation, one or more of the exercise devices may be combined with the exercise server 120.

In one implementation, some or all of the exercise devices 130A-130Z may include local storages 134A-134Z. Each of the local storages 134A-134Z may store data before, after, and during the execution of an exercise program. In one implementation, one or more of the local storages 134A-134Z may store data as it is generated during an exercise session. For example, local storage 134A may store handle displacement, handle speed (e.g., handle displacement versus time), resistance (e.g., generated by the motor), applied force (e.g., force applied by the user), etc. recorded as a user performs an exercise with the exercise device 130A. In one implementation, one or more of exercise devices 130A-130Z may download exercise program data from one or more of the client devices 110A-110Z and/or the exercise server 120. For example, the motor control unit 132A may be a programmable device (e.g., an FPGA) that executes the exercise program in accordance with the downloaded exercise program data stored in the local storage 134A. The exercise program data may include instructions that cause the motor control unit 132A to actuate a motor of the exercise device 130A, lock the motor, measure or record data (e.g., force applied to a component of the exercise device 130A, speed of the component, displacement of the component, etc.), transmit data (e.g., to one or more of the client devices 110A-110Z and/or the exercise server 120), etc.

In one implementation, the data store 140 may be a memory (e.g., random access memory), a cache, a drive (e.g., a hard drive), a flash drive, a database system, or another type of component or device capable of storing data. The data store 140 may also include multiple storage components (e.g., multiple drives or multiple databases) that may also span multiple computing devices (e.g., multiple server computers), and may be cloud-based. In some implementations, the data store 140 may be a part of the exercise server 120. In some implementations, the data store 140 may be distributed among and accessible to one or more of the client devices 110A-110Z, the exercise server 120, and one or more of the exercise devices 130A-130Z. One or more of the devices of the system architecture 100 may utilize the data store 140 to store public and private data, and the data store 140 may be configured to provide secure storage for private data.

In one implementation, the network 150 may include a public network (e.g., the Internet), a private network (e.g., a local area network (LAN) or wide area network (WAN)), a wired network (e.g., Ethernet network), a wireless network (e.g., an 802.11 network or a Wi-Fi network), a cellular network (e.g., a Long Term Evolution (LTE) network), routers, hubs, switches, server computers, and/or a combination thereof. In some implementations, the network 150 may be a combination of different types of networks. In one implementation, one or more of the exercise devices 130A-130Z may communicate directly with one or more of the client devices 110A-110Z. For example, the exercise device 130A may include a Bluetooth device that sends/receives data to/from the client device 110A.

Figure 2A:
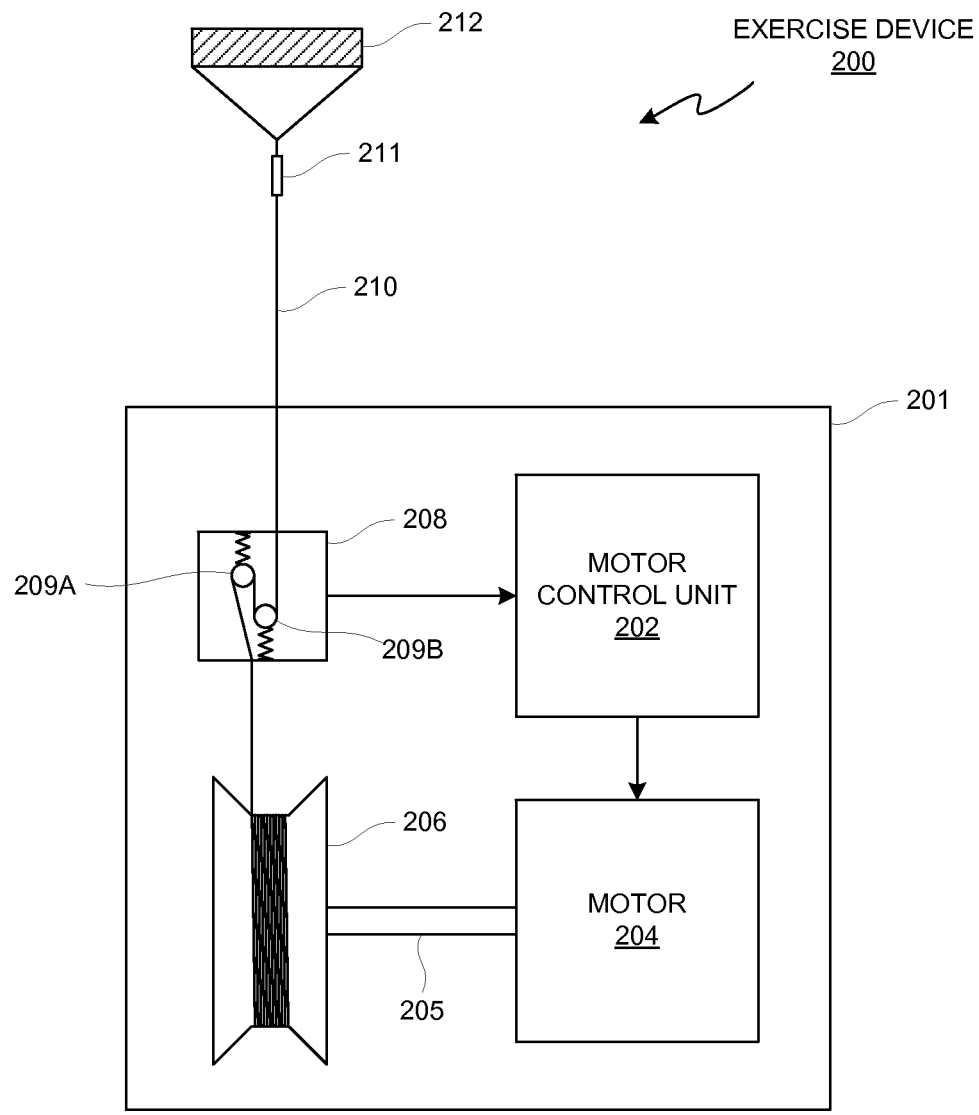
FIG. 2A is a block diagram illustrating features of an exercise device in accordance with an implementation of the disclosure.

FIG. 2A is a block diagram illustrating features of an exercise device 200 in accordance with an implementation of the disclosure. The exercise device 200 may be the same as or similar to any of the exercise devices 130A-130Z described with respect to FIG. 1. As illustrated in FIG. 2A, the exercise device 200 includes a housing 201, which contains a motor control unit 202, a motor 204 (which may contain one or more sets of gears), a spool 206, and a tension gauge 208. The motor 204 may be operatively coupled to the spool 206 by a drive shaft 205 that can rotate or lock the spool 206. A tension line 210 may be wrapped around the spool 206 and fed through the tension gauge 208. At least a portion of the tension line 210 is contained within the housing 201 at any given time, while a remaining portion is outside of the housing 201. A first end of the tension line 210 may be connected to the spool 206, while a second end is connected to a handle 212. The handle 212 may be held by a user while performing an exercise, as illustrated in FIGS. 2B and 2C.

In one implementation, the motor control unit 202 is communicatively coupled to the motor 204. The motor control unit may be similar to any of the motor control units 132A-132Z described with respect to FIG. 1. The motor control unit 202 may cause the motor 204 to rotate the spool 206 in two directions, lock its rotation, and/or adjust a speed of rotation. In one implementation, the tension gauge 208 is communicatively coupled to the motor control unit 202. The tension gauge 208 may measure a tension of the tension line 210 and a rotational speed of the spool 206. The motor control unit 202 may use measurement data received in real-time from the tension gauge 208 as feedback for controlling the motor 204 in order to adjust a location of the handle 212, create slack in the tension line 210, adjust a resistance of the exercise device 200 (e.g., resistance experienced by a user who is pulling on the handle 212), regulate and/or enforce a speed of an exercise, limit a range of motion of an exercise, etc. It is noted that the use of the tension line 210, tension gauge 208, and spool 206 are illustrative, and that the exercise device 200 may utilize mechanical arms, weight stacks (e.g., which may contain computer-controlled mechanical components that automatically adjust the resistance of the weight stack), other components, or combinations thereof, as would be appreciated by one of ordinary skill in the art.

In one implementation, the motor control unit 202 may measure a force applied by a user to the handle 212. In one implementation, the force may be measured by measuring a counter-force generated by the motor 204 to balance the applied force. For example, the motor control unit 202 may measure a motor current that drives the motor 204, and compute the force based on the measured motor current. In one implementation, the applied force may be measured using spring loaded pulleys 209A and 209B of the tension gauge 208. For example, the applied force to the tension line 210 may cause the spring loaded pulleys 209A and 209B to be displaced, providing a measurable signal to the motor control unit 202 that may be used to compute the applied force. In one implementation, the tension line 210 includes a load cell 211 that may be used to transduce the applied force into an electrical signal. In one implementation, the load cell 211 may be communicatively coupled to the motor control unit 202. For example, the load cell 211 may connect directly to the tension gauge 208 and/or the motor control unit 202 with a wired connection. As another example, a transmitter may be located in the handle 212 that transmits the electrical signal measured by the load cell 211 to the motor control unit 202 wirelessly. In some implementations, the motor control unit 202 may use some or all of the aforementioned methods for measuring the applied force, as well as other suitable methods as would be appreciated by one of ordinary skill in the art.

In one implementation, the housing 201 encloses less than all of the components (e.g., the motor control unit 202, the motor 204, the drive shaft 205, the spool 206, and the tension gauge 208) of the exercise device 200. In one implementation, the housing 201 is omitted entirely. In one implementation, the housing encloses additional components not shown. For example, a client device (e.g., any of client devices 110A-110Z) may be combined with the exercise device 200 such that a display of the client device is integrally formed into an exterior surface of the housing 201. In one implementation, the exercise device 200 may include additional motors, spools, tension gauges, and tension lines. In one implementation, multiple exercise devices may be combined or arranged together as an "exercise system". In one implementation, the exercise system includes one or more client devices (e.g., client devices 110A-110Z) and/or one or more exercise servers (e.g., exercise server 120).

FIG. 2B illustrates an exercise system 220 according to an implementation of the disclosure. The exercise system 220 includes exercise devices 221A and 221B, each including tension lines 222A and 222B, respectively, and handles 224A and 224B, respectively. The exercise devices 221A and 221B may be the same or similar to the exercise device 200 described with respect to FIG. 2A. Each of the exercise devices 221A and 221B are disposed on opposite ends of an upper surface of a platform 226. In some implementations, other arrangements of the exercise devices 221A and 221B may be used. For example, the platform 226 may be omitted in favor of using a frame-like structure to which the exercise devices 221A and 221B are attached. In some implementations, additional exercise devices may be used. In some implementations, one exercise device (e.g., 221A) may be included depending on the exercise. In some implementations, one or more of the exercise devices 221A and 221B are removable. In some implementations, the platform 226 may include multiple attachment locations for attaching exercise devices. In some implementations, the positions of the exercise devices 221A and 221B may be adjustable on the platform 226.

FIG. 2B depicts a user 223 standing on the platform 226 while gripping and pulling handles 224A and 224B to perform an exercise (e.g., standing curls). In one implementation, the exercise system 220 may also include a client device (e.g., one of client devices 110A-110Z), which may be used/operated by the user 223 while the user is performing an exercise with exercise system 220. The client device may include a display screen, and may be placed in front of the user to guide the user 223 while performing the exercise. In one implementation, the exercise system 220 may include a mount for placing the client device in front of the user 223. In one implementation, the user 223 may wear the client device while performing the exercise. For example, when wearing the client device, the client device may provide audio and/or tactile cues (e.g., vibrations) to guide the user 223 through the exercise.

FIG. 2C illustrates an exercise system 230 according to another implementation of the disclosure. Exercise system 230 is similar to the exercise system 220, except that exercise system 220 includes a single exercise device 231 located at a central region of a platform 236. The exercise device 231 includes two tension lines 232A and 232B, which may each be connected to spools and one or more motors (e.g., a single motor that drives both spools or a motor for each spool). The tension lines 232A and 232B may be directed below the platform 236, to outer edges of the platform 236, and up through the platform 236 by a plurality of pulleys 238A-238D, as illustrated.

In one implementation, one or more of the exercise systems 220 and 230 (as well as variations of the exercise systems 220 and 230) include heart rate monitoring capabilities. In one implementation, heart rate sensors are built into handles of the exercise device (e.g., handles 224A, 224B, 234A, and 234B), and the handles may be electronically coupled together. The handles may transmit heart rate signals through their respective tension lines to motor control units within the exercise devices, or with other wired connections. In one implementation, the handles may include transmitters that transmit the heart rate signals wirelessly (e.g., to one or more client devices and/or one or more motor control units). In one implementation, a heart rate monitor may be worn the user (e.g., user 223 and/or 233). The heart rate monitor may be a client device, or be attached to a client device. In one implementation, a measured heart rate may serve as an indicator to vary parameters of a currently executed exercise program. For example, if the measured heart rate exceeds a threshold value, the exercise system may reduce resistance of one or more exercise devices dynamically during the execution of the exercise program to keep the user's heart rate within a predetermined range. Similarly, if the measured heart rate is below a threshold value (e.g., after a time duration of performing the exercise and/or it is determined that the heart rate has minimally increased from a starting heart rate), the exercise system may dynamically increase the resistance of one or more exercise devices.

In one implementation, two or more exercise devices may be used to simultaneously measure and compare the strength of a user's limbs to determine if there are strength imbalances between the limbs. For example, the exercise device 220A may measure a force applied by the user's right arm while the exercise device 220B measures a force applied by the user's left arm (e.g., while trying to determine a maximum amount of force that the user is capable of applying by each arm). An imbalance percentage may correspond to an absolute difference between the two forces divided by the larger of the two forces. In one implementation, the system may determine that an imbalance exists if the imbalance percentage is 5% or greater. In one implementation, the system may determine that an imbalance exists if the imbalance percentage is 10% or greater. In one implementation, the system may determine that an imbalance exists if the imbalance percentage is 15% or greater. In one implementation, a message may be generated (e.g., generated for display by one of the client devices 110A-110Z) that indicates to the user that an imbalance was detected. In one implementation, a resistance correction may be applied to correct the imbalance. For example, if the left arm is weaker than the right arm, a resistance experienced by the left arm may be decreased based on the resistance correction (e.g., decreased with respect to the resistance experienced by the right arm). In one implementation, the resistance correction may be the same as the imbalance percentage.

Figure 3:
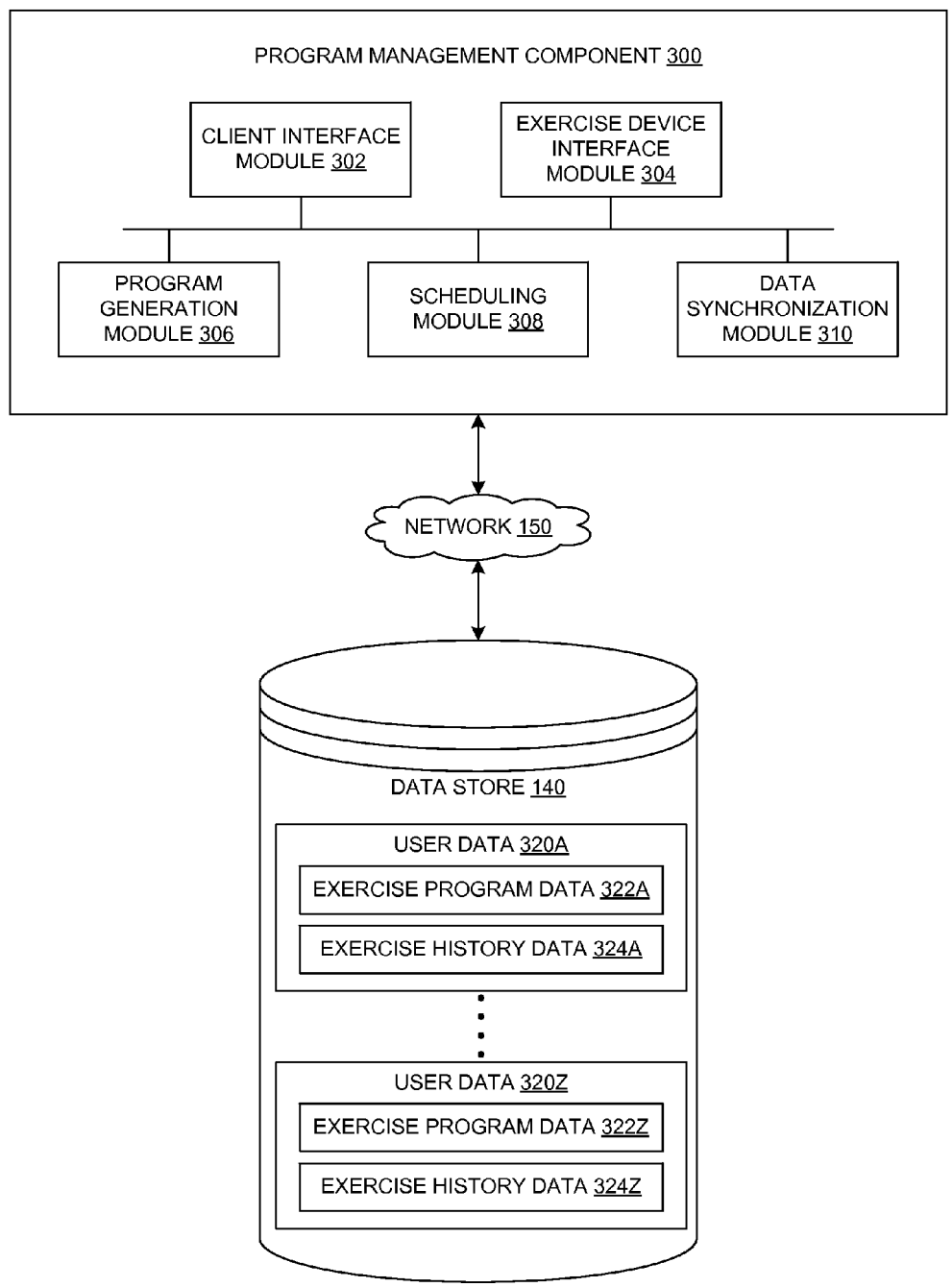
FIG. 3 is a block diagram illustrating features of a program management component according to an implementation of the disclosure.

FIG. 3 is a block diagram illustrating features of a program management component 300 in accordance with an implementation of the disclosure. The program management component 300 may be the same as its identically named counterpart of FIG. 1. In one implementation, the program management component 300 includes a client interface module 302, an exercise device interface module 304, a program generation module 306, a scheduling module 308, and a data synchronization module 310. More or less components may be included in the program management component 300 without loss of generality. For example, two or more of the modules may be combined into a single module, or one of the modules may be divided into two or more modules. In one implementation, one or more of the modules may reside on different computing devices (e.g., different server computers, on a client device, distributed among multiple client devices, etc.). For illustrative purposes, the program management component 300 is described as being implemented by the exercise server 120 of FIG. 1, but it may be implemented at least partially by any of the client devices 110A-110Z and any of the exercise devices 130A-130Z. For example, a client device (e.g., client device 110A) may be programmed to perform some or all of the functions of the program management component 300. When the program management component 300 is implemented on a client device, any functions described with respect to the program management component 300 that "receive", "transmit", "generate", "retrieve", "identify", "determine", "select", etc., are understood to refer to functions performed by sub-systems or sub-modules within the client device rather than across a network (e.g., the network 150), as would be appreciated by one of ordinary skill in the art.

In some implementations, if the program management component 300 is implemented on an exercise server (e.g., the exercise server 120), the program management component 300 may utilize the client interface module 302 to send/receive data to/from one or more client devices (e.g., client devices 110A-110Z) and/or exercise devices (e.g., exercise devices 130A-130Z). The client interface module 302 may store/retrieve user data 320A-320Z in/from the data store 140 (e.g., via the network 150). For example, the user data 320A may correspond to a first user, the user data 320B may correspond to a second user, etc. Each of user data 320A-320Z may store exercise program data 322A-322Z, respectively, and exercise history data 324A-324Z, respectively. For example, exercise program data 322A may include, but is not limited to, parameters related to a particular exercise program of a user (e.g., user height, weight, age, sex, exercise goal, etc.), one or more set tables that lists exercises (along with their associated resistances, repetitions (also referred to herein as "reps"), and numbers of sets), and exercise program schedule data (e.g., dates and times at which exercises are to be performed). In addition, the exercise program data 322A may also include data indicative of a maximum resistance at which a user can successfully perform a single repetition (referred to herein as "one-rep maximum" data). As a further example, exercise history data 324A may include, but is not limited to, data related to previously performed exercises and whether or not the previously performed exercises were successfully performed. In one implementation, some or all of user data 320A-320Z may be stored on a respective client device or exercise device (e.g., on one or more local storages 114A-114Z and/or local storages 134A-134Z). In one implementation, the client interface module 302 may work in conjunction with the data synchronization module 310 to synchronize data stored across each of the local storages and the data store 140 in response to the data synchronization module 310 determining that updated data has become available.

In some implementations, if the program management component 300 is implemented on one or more client devices and/or one or more exercise devices, the client interface module 302 may be omitted or implemented as a local user interface (e.g., one of user interfaces 112A-112Z). In such implementations, user data may still be stored and maintained in the data store 140 or be locally maintained (e.g., in one of local storages 114A-114Z and/or local storages 134A-134Z).

In one implementation, the program management component 300 utilizes the exercise device interface module 304 to send/receive data to/from one or more motor control units of exercise devices (e.g., one or more of the motor control units 132A-132Z). In some implementations, the exercise device interface module 304 may directly instruct the one or more motor control units to execute an exercise program (e.g., by adjusting resistance, displacing handles, etc.). In some implementations, the exercise device interface module 304 may transmit exercise program data to the one or more motor control units, which may be downloaded and stored by the one or more motor control units (e.g., using one or more of the local storages 134A-134Z) and executed. In one implementation, the one or more motor control units may receive a signal from the exercise device interface module to execute the exercise program.

In one implementation, the program management component 300 utilizes the program generation module 306 to automatically generate an exercise program for a user. The functionality of the program generation module 306 will be described in detail below with respect FIGS. 4-6.

In one implementation, the program management component 300 utilizes the scheduling module 308 to generate exercise program schedule data for a user. The functionality of the scheduling module 308 will be described in detail below with respect FIG. 5.

Figure 4:
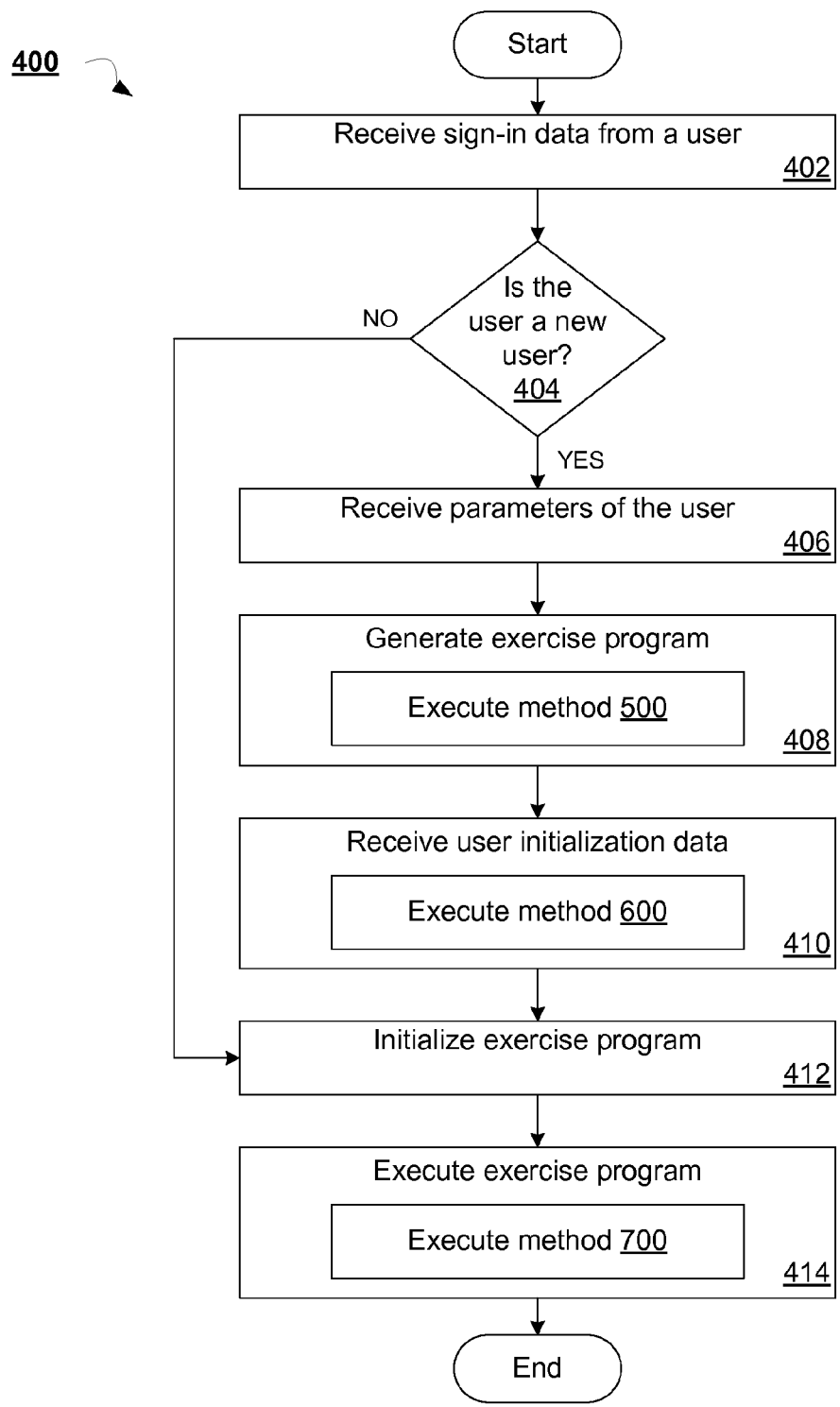
FIG. 4 is a flow diagram illustrating a method for generating an exercise program according to an implementation of the disclosure.

FIG. 4 is a flow diagram illustrating a method 400 for generating an exercise program according to an implementation of the disclosure. The method 400 may be performed by processing logic that includes hardware (e.g., circuitry, dedicated logic, programmable logic, microcode, etc.), software (e.g., instructions run on a processing device to perform hardware simulation), or a combination thereof. In one implementation, the method 400 may be performed by the program management component 300, which may be implemented by one or more of the client devices 110A-110Z, the exercise server 120, one or more of the exercise devices 130A-130Z, or combinations thereof. In one implementation, the method 400 may be performed at least partially by a user interface of a client device (e.g., any of user interfaces 112A-112Z of client devices 110A-110Z, respectively) as described with respect to in FIG. 1.

Referring to FIG. 4, the method 400 begins at block 402 where sign-in data is received from a user. For example, a user may use a client device (e.g., one of client devices 110A-110Z) to sign into his/her exercise program account (which may correspond to one or more of user data 320A-320Z). For example, the exercise program account may be maintained by an exercise server (e.g., exercise server 120). In some implementations, the exercise program account may be maintained locally on the client device. In one implementation, block 402 is performed by the client interface module 302.

At block 404, a determination is made as to whether the user is a new user. If it is determined that an exercise program account does not exist for the user, the method 400 proceeds to block 406. Otherwise, the method 400 proceeds to block 412.

At block 406, a plurality of parameters of the user are received (e.g., as user inputs to a client device). The parameters may include, but are not limited to, age, weight, height, sex, any pre-existing medical conditions or indicators (e.g., the user has congestive heart failure, the user is a diabetic, the user is or is not healthy enough for sexual intercourse, etc.), a goal of the exercise program (e.g., maintain current muscle, muscle growth, athlete/high performance training, etc.), etc. In one implementation, the parameters may be received via a user interface of a client device (e.g., one of user interfaces 112A-112Z). In one implementation, the parameters may be received directly at an exercise server (e.g., the exercise server 120), or received by a client device and transmitted to the exercise server (e.g., via the network 150). In one implementation, the parameters may be received from more than one client device and/or the exercise server. For example, some of the parameters may be received by a first client device (e.g., from the user who will be performing the exercises), and other parameters may be received by a second client device or received directly at the exercise server (e.g., from a doctor, therapist, insurance provider, personal trainer, etc.). In one implementation, the parameters may be stored in a data store (e.g., stored as user data 320A of the data store 140).

At block 408, an exercise program is generated (e.g., based at least partially on the plurality of parameters. The exercise program includes a plurality of exercises (e.g., stored as a data structure). In one implementation, block 408 is performed by the program generation module 306. In one implementation, block 408 may further execute a method 500, which is described below with respect to FIG. 5.

Figure 5:
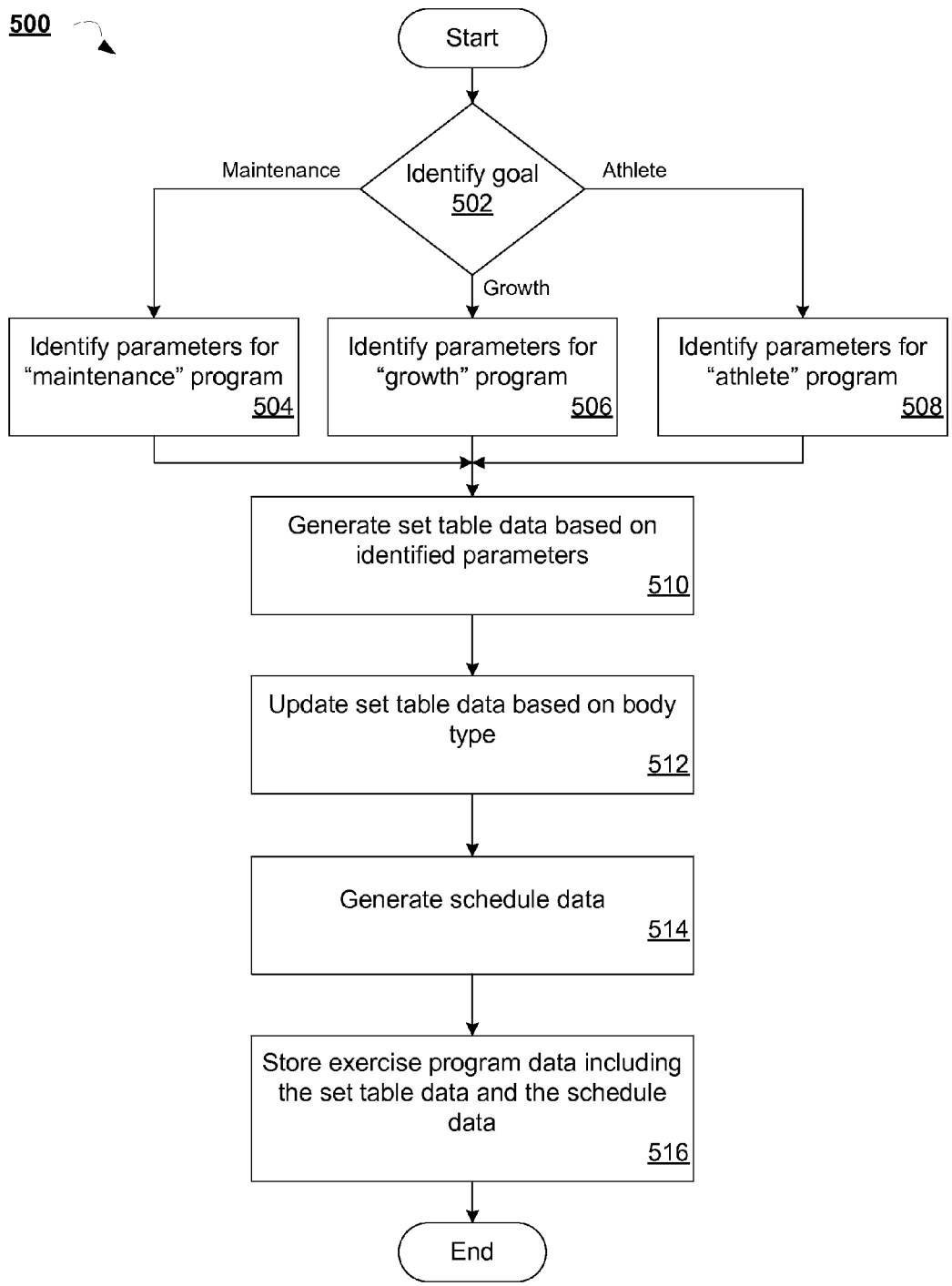
FIG. 5 is a flow diagram illustrating a method for scheduling an exercise program according to an implementation of the disclosure.

Reference is now made to FIG. 5, which is a flow diagram illustrating the method 500 for scheduling an exercise program according to an implementation of the disclosure. The method 500 may be performed by processing logic that includes hardware (e.g., circuitry, dedicated logic, programmable logic, microcode, etc.), software (e.g., instructions run on a processing device to perform hardware simulation), or a combination thereof. In one implementation, the method 500 may be performed by the program management component 300, which may be implemented by one or more of the client devices 110A-110Z, the exercise server 120, one or more of the exercise devices 130A-130Z, or combinations thereof. In one implementation, the method 500 may be performed at least partially by a user interface of a client device (e.g., any of user interfaces 112A-112Z of client devices 110A-110Z, respectively) as described with respect to in FIG. 1.

Referring to FIG. 5, the method 500 begins at block 502, where a goal of a user is identified. For example, the goal may have been designated by the user as one of the parameters received during the execution of block 406 of the method 400. In one implementation, the goal may correspond to, but is not limited to, muscle maintenance (to maintain current muscle with little to no growth), muscle growth (to increase the amount of muscle), and athlete/high performance (to increase muscle growth and endurance). In some implementations, other goals may be designated by the user.

In one implementation, if the goal is muscle maintenance, then method 500 proceeds to block 504 where parameters corresponding to a maintenance-specific exercise program are identified (e.g., high number of reps, low resistance). If the goal is muscle growth, then method 500 proceeds to block 506 where parameters corresponding to a growth-specific exercise program are identified (e.g., medium number of reps, high resistance). If the goal is athlete/high performance, then method 500 proceeds to block 508 where parameters corresponding to an athlete-specific exercise program are identified (e.g., high number of reps, high resistance). The parameters of each of the exercise programs may be identified, for example, by retrieving the parameters from a data store (e.g., the data store 140), an exercise server (e.g., the exercise server 120), or another source.

At block 510, set table data is generated based on the identified parameters. In one implementation, the set table data may be in the form of a data structure that includes a plurality of exercises, with each exercise having an associated number of sets, an associated number of reps per set, an associated resistance (e.g., force), and an associated repetition speed (e.g., amount of time per rep). The set table data may also include rest time durations that are to occur between each exercise set and/or rest time durations that are to occur between each exercise. In one implementation, the generated set table data may be stored with other data associated with the user (e.g., stored as user data 320A in the data store 140).

At block 512, the set table data is updated based on a body type of the user, and/or other parameters of the user. The body type may be ectomorph, endomorph, mesomorph, or combinations thereof.

At block 514, schedule data is generated. In one implementation, the schedule data is generated by the scheduling module 308. The schedule data may include a plurality of workout sessions that are scheduled for different days. The workout sessions may include a single exercise or multiple exercises (e.g., as defined in the set table data). In some implementations, the schedule data is generated such that there is a minimum number of days between sessions that contain the same exercise, so as to provide recovery time for the muscle groups that are worked by the exercise. In one implementation, the scheduling module 308 may compute a total workout time for each of the plurality of workout sessions. For example, a total workout time may take into account the number of exercises to be performed in the workout session, an amount of repetitions, a repetition speed, a number of sets, a rest time duration between the sets, a rest time duration between the exercises, a time duration for initialization, etc. In one implementation, the schedule data is generated based at least partially on a goal of the user. For example, a user may have specified a goal to increase leg strength. Accordingly, the scheduling module 308 may group leg exercises together in scheduled exercise sessions such that leg exercises occur more frequently in the exercise program than other types of exercises.

In one implementation, calendar data corresponding to a calendar of the user may be received (e.g., imported by one of client devices 110A-110Z, one of the exercise devices 130A-130Z, and/or the exercise server 120). In some implementations, the calendar data may be retrieved from a remote source (e.g., an e-mail server), or may be retrieved from local storage. In one implementation, the schedule data may be generated based on the received calendar data. For example, the schedule data may be generated to avoid conflicts (e.g., scheduling conflicts) with the calendar data. In one implementation, reserved blocks of time may be identified in the calendar data, and the schedule data may schedule workout sessions that avoid overlap with the reserved blocks of time. In one implementation, the user may schedule the workout sessions directly (e.g., with the user interface 112A of the client device 110A). In one implementation, the user may provide one or more user-preferred times that he/she would like to exercise (e.g., which may indicate one or more of preferred start and end times), and the calendar data may be generated based at least partially on the one or more user-preferred times.

At block 516, exercise program data is stored (e.g., stored locally on one of client devices 110A-110Z, stored in the data store 140, etc.), with the exercise program data containing the set table data and the schedule data. The method 500 ends after block 516.

Referring once again to FIG. 4, after executing the method 500, the method 400 proceeds to block 410 where user initialization data is received. In one implementation, block 410 is performed by the client interface module 302. In one implementation, block 410 may further execute a method 600, which is described below with respect to FIGS. 6A and 6B.

Figure 6A:
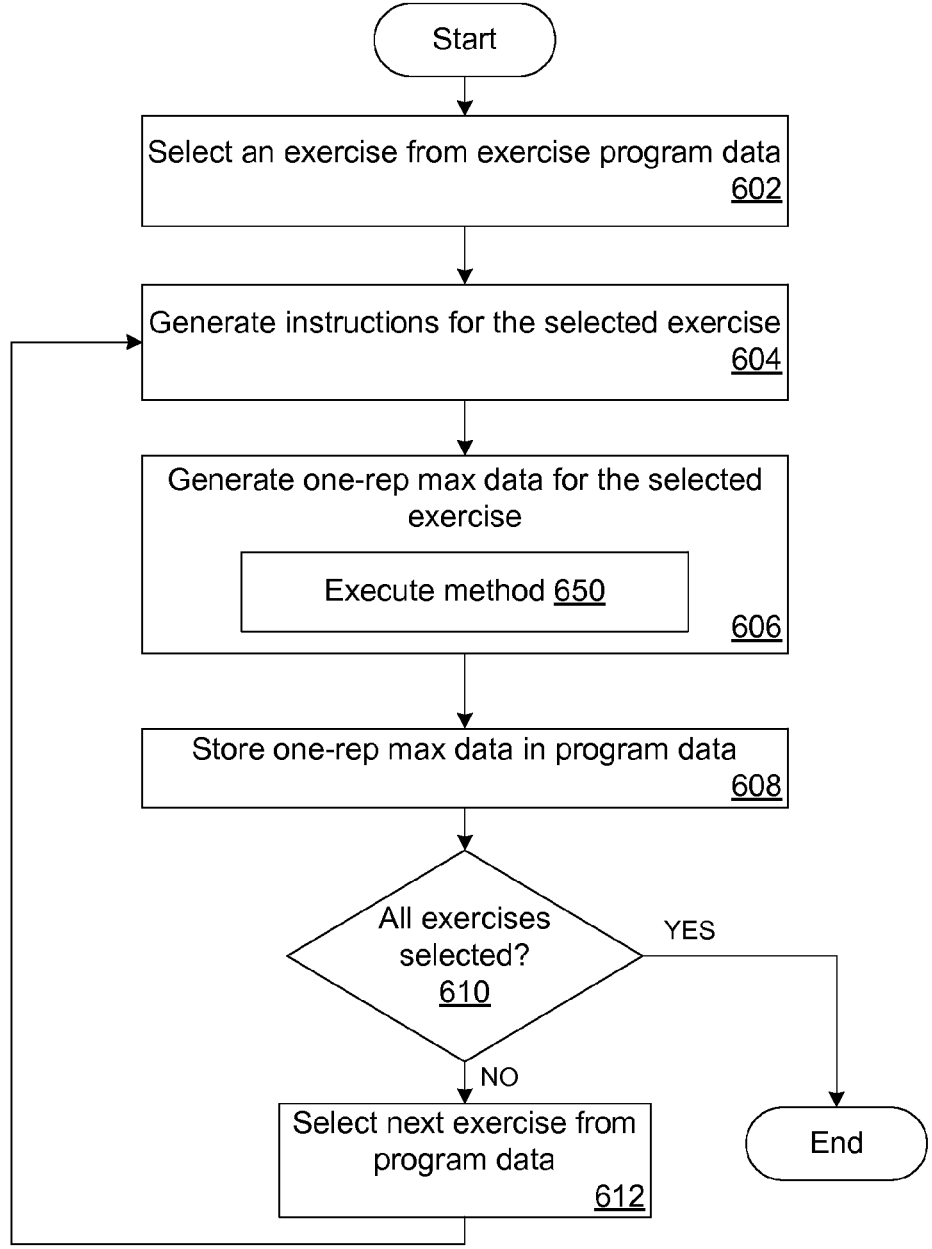
FIG. 6A is a flow diagram illustrating a method for calibrating an exercise program according to an implementation of the disclosure.
Figure 6B:
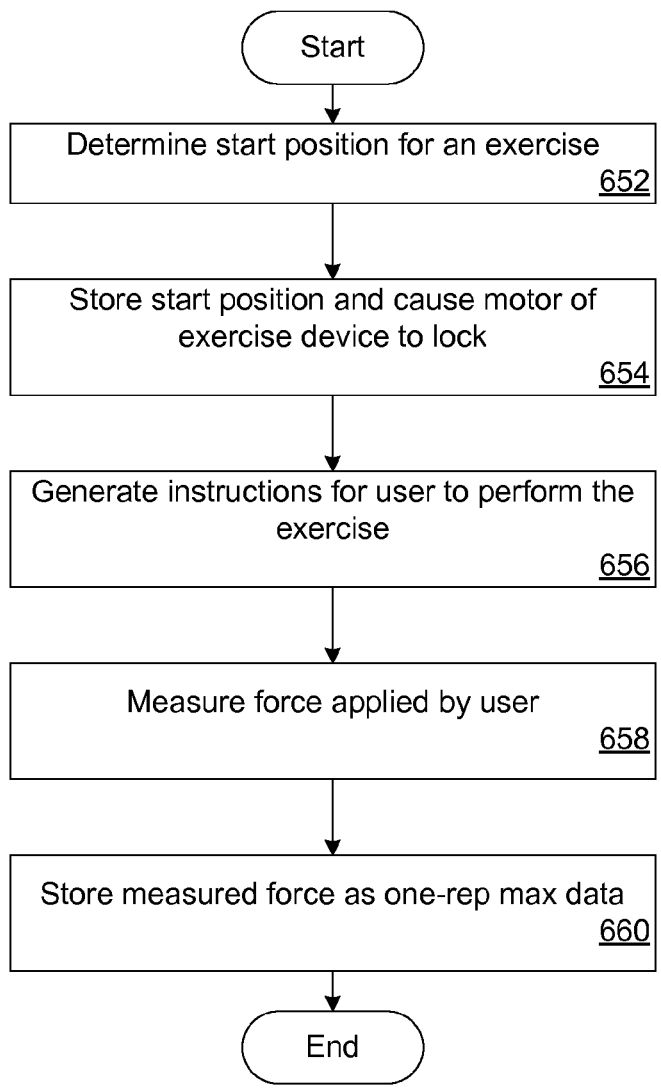
FIG. 6B is a flow diagram illustrating a method for determining a maximum amount of resistance a user is capable of applying to an exercise device according to an implementation of the disclosure.

Reference is now made to FIGS. 6A and 6B, which are flow diagrams illustrating, respectively, the method 600 for calibrating an exercise program according to an implementation of the disclosure and a method 650 for determining a maximum amount of resistance a user is capable of applying to an exercise device according to an implementation of the disclosure. The methods 600 and 650 may each be performed by processing logic that includes hardware (e.g., circuitry, dedicated logic, programmable logic, microcode, etc.), software (e.g., instructions run on a processing device to perform hardware simulation), or a combination thereof. In some implementations, the methods 600 and 650 may each be performed by the program management component 300, which may be implemented by one or more of the client devices 110A-110Z, the exercise server 120, one or more of the exercise devices 130A-130Z, or combinations thereof. In some implementations, the methods 600 and 650 may each be performed at least partially by a user interface of a client device (e.g., any of user interfaces 112A-112Z of client devices 110A-110Z, respectively) as described with respect to in FIG. 1.

Referring to FIG. 6A, the method 600 is initiated at block 602, where an exercise is selected from the exercise program data. For example, the selected exercise may be selected from the table set data in a sequential manner.

At block 604, instructions for a user to perform the selected exercise are generated (e.g., with one of client devices 110A-110Z and/or the exercise devices 130A-130Z). For example, if the selected exercise is a squat, a client device of the user may generate for display a visual depiction of how the user is to stand while prior to performing the squat and how to hold on to handles of one or more exercise devices. The client device may also generate for display a video of an individual performing squats. In some implementations, the client device may generate audio instructions. In one implementation, the client device may generate an indication as to when the exercise is to be performed (e.g., a countdown).

At block 606, one-rep maximum data is generated for the selected exercise. In one implementation, block 606 is performed by the program generation module 306. In one implementation, block 606 may further execute the method 650, which is described below with respect to FIG. 6B.

Referring to FIG. 6B, the method 650 begins at block 652 where a start position is determined for the exercise. In one implementation, the start position may be determined by prompting the user (e.g., using the client device) to assume a position for performing the exercise while holding onto one or more handles of respective exercise devices, and then determining a relative displacement of the one or more handles. At block 654, the start position is stored (e.g., locally or in the data store 140) and one or more motors of respective exercise devices are locked. In one implementation, the client device causes the one or more motors to be locked by transmitting an indication to one or more respective motor control units of the one or more motors.

At block 656, instructions are generated that instruct the user to perform a repetition of the exercise while exerting as much force as possible. In one implementation, the motor may generate a counter-force to attempt to balance the force applied by the user, while also allowing the user to perform the full range of motion of the repetition. At block 658, force data (e.g., the force applied by the user) is measured (e.g., using one or more tension gauges, such as tension gauge 208) during the repetition, and a one-rep maximum is computed. In one implementation, a one-rep maximum is computed by averaging the force data over a duration of the repetition (e.g., an average force). At block 660, the computed one-rep maximum is stored as one-rep maximum data (e.g., in the data store 140).

Referring once again to FIG. 6A, after executing the method 650, the method 600 proceeds to block 608 where the generated one-rep maximum data is stored (e.g., stored with user data 320A in the data store 140). In one implementation, the one-rep maximum data is stored with set table data. In one implementation, a resistance is computed for the selected exercise based at least partially on the one-rep maximum data for the selected exercise and based at least partially on one or more parameters of the user (e.g., exercise goal, body type, etc.). For example, if the exercise goal is "maintenance", the computed resistance may be 70% of a one-rep maximum resistance. As another example, if the exercise goal is "growth", the computed resistance may be 80% of a one-rep maximum resistance. As another example, if the exercise goal is "athlete", the computed resistance may be 90% of a one-rep maximum resistance. In one implementation, the computed resistance may be added to the set table data, or may replace a previously stored resistance in the set table data, for the selected exercise. In one implementation, the computed resistance may be designated as an initial resistance value of the exercise program (e.g., the designation may be stored as exercise history data 324A), which may be used downstream when updating the exercise program data.

At block 610, a determination is made as to whether all exercises have been selected (e.g., whether one-rep maximum data has been generated for all exercises in the exercise program). If it is determined that not all exercises have been selected, then the method 600 proceeds back to block 612 in which the next exercise is selected. Otherwise, the method 600 ends.

Tables 1-4 illustrate set table data generated for exercise programs based on different user parameters. It is noted that the exercises listed are illustrative, and any suitable number and type of exercise may be included. Moreover, the exercises may be performed at different times according to schedule data generated for the exercise program. In each table, one-rep maxima and resistances are given in pounds, and repetition speed is given in seconds per rep. In one implementation, one or more of Tables 1-4 may have been generated as set table data as a result of executing methods 500, 600, and 650 (e.g., using the program generation module 306).

Table 1 illustrates a set table for a maintenance program, and Table 2 illustrates a set table for a growth program. It is noted that the initial parameters differ between Tables 1 and 2 in terms of resistance, reps, sets, and rep speed. For example, the resistances correspond to 60% and 80% of the respective one-rep maxima of Tables 1 and 2. Table 3 illustrates a set table for a growth program generated for a user with an endomorphic body type. Table 3 is similar to Table 2 in terms of one-rep maxima for each exercise, except that Table 3 has taken into account the user's body type (e.g., which may have been entered as a parameter at block 406). For example, for a user with a mesomorphic body type, the set table data may include resistances that are 50% of the respective one-rep maxima for each exercise, a higher number of reps, and faster reps. This may account for a user that is out of shape and/or lacks sufficient strength to perform the exercises compared to another individual (e.g., a mesomorph) who may be naturally suited for high resistance training. Table 4 illustrates a set table for an athlete program generated for a user with a mesomorphic body type. The resistances for each exercise are 90% of the respective one-rep maxima of each exercise, and the number of reps for each exercise may be higher than for a growth program. In some implementations, and as illustrated in Table 4, a user who selects his/her goal as "athlete" may be provided with additional options to adjust/edit the generated exercise program. For example, a user that is a high performance athlete may specify additional goals (such as "increase upper body strength"), which may result in a heavier focus on upper body exercises, as shown in Table 4.

TABLE 1

Example Maintenance Program Set Table

| Exercise | One-Rep Max. | Resistance | Reps | Sets | Rep Speed |
|---|---|---|---|---|---|
| Squats | 150 | 90 | 10 | 2 | 4 |
| Curls | 80 | 48 | 10 | 2 | 4 |
| Shoulder Press | 60 | 36 | 10 | 2 | 4 |

TABLE 2

Example Growth Program Set Table

| Exercise | One-Rep Max. | Resistance | Reps | Sets | Rep Speed |
|---|---|---|---|---|---|
| Squats | 150 | 120 | 8 | 3 | 8 |
| Curls | 80 | 64 | 8 | 3 | 8 |
| Shoulder Press | 60 | 48 | 8 | 3 | 8 |

TABLE 3

Example Growth Program Set Table for an Endomorph

| Exercise | One-Rep Max. | Resistance | Reps | Sets | Rep Speed |
|---|---|---|---|---|---|
| Squats | 150 | 75 | 20 | 3 | 4 |
| Curls | 80 | 40 | 20 | 3 | 4 |
| Shoulder Press | 60 | 30 | 20 | 3 | 4 |

TABLE 4

Example Athlete Program Set Table for a Mesomorph

| Exercise | One-Rep Max. | Initial Res. | Reps | Sets | Rep Speed |
|---|---|---|---|---|---|
| Flies | 120 | 108 | 12 | 3 | 8 |
| Curls | 80 | 72 | 12 | 3 | 8 |
| Shoulder press | 120 | 108 | 12 | 3 | 12 |
| Tricep extensions | 80 | 72 | 12 | 3 | 8 |

Referring once again to FIG. 4, after executing the method 600, the method 400 proceeds to block 412 where the exercise program is initialized. In one implementation, the exercise program may be initialized by the user selecting an option (e.g., using one of the client devices 110A-110Z) indicating that he/she wishes to begin the exercise program. In one implementation, exercise program data may be downloaded to one or more exercise devices of the user.

At block 414, the exercise program is executed. In one implementation, block 408 is performed by the exercise device interface module 304. In one implementation, block 414 may further execute a method 700, which is described below with respect to FIG. 7A.

Figure 7A:
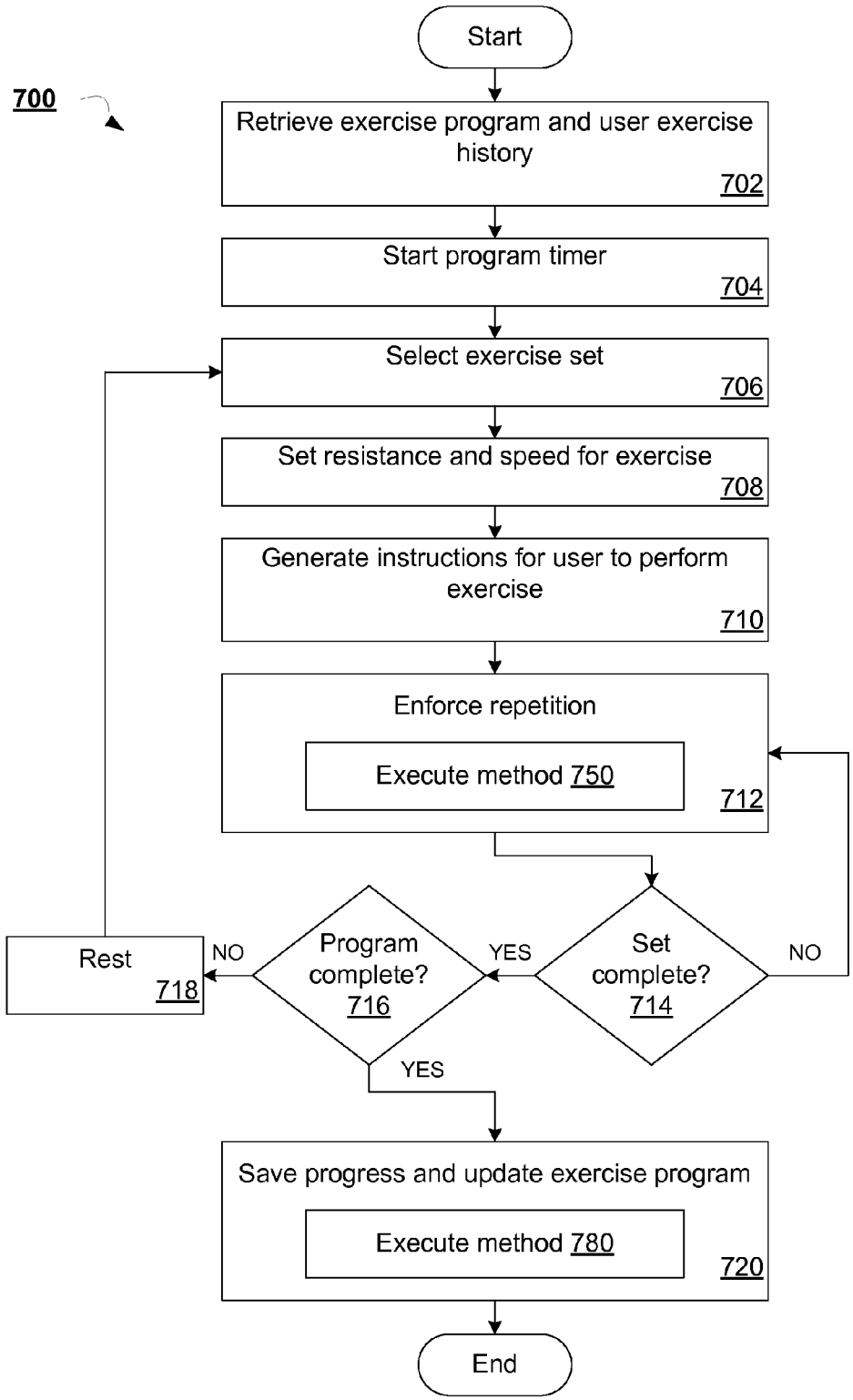
FIG. 7A is a flow diagram illustrating a method for executing an exercise program according to an implementation of the disclosure.
Figure 7B:
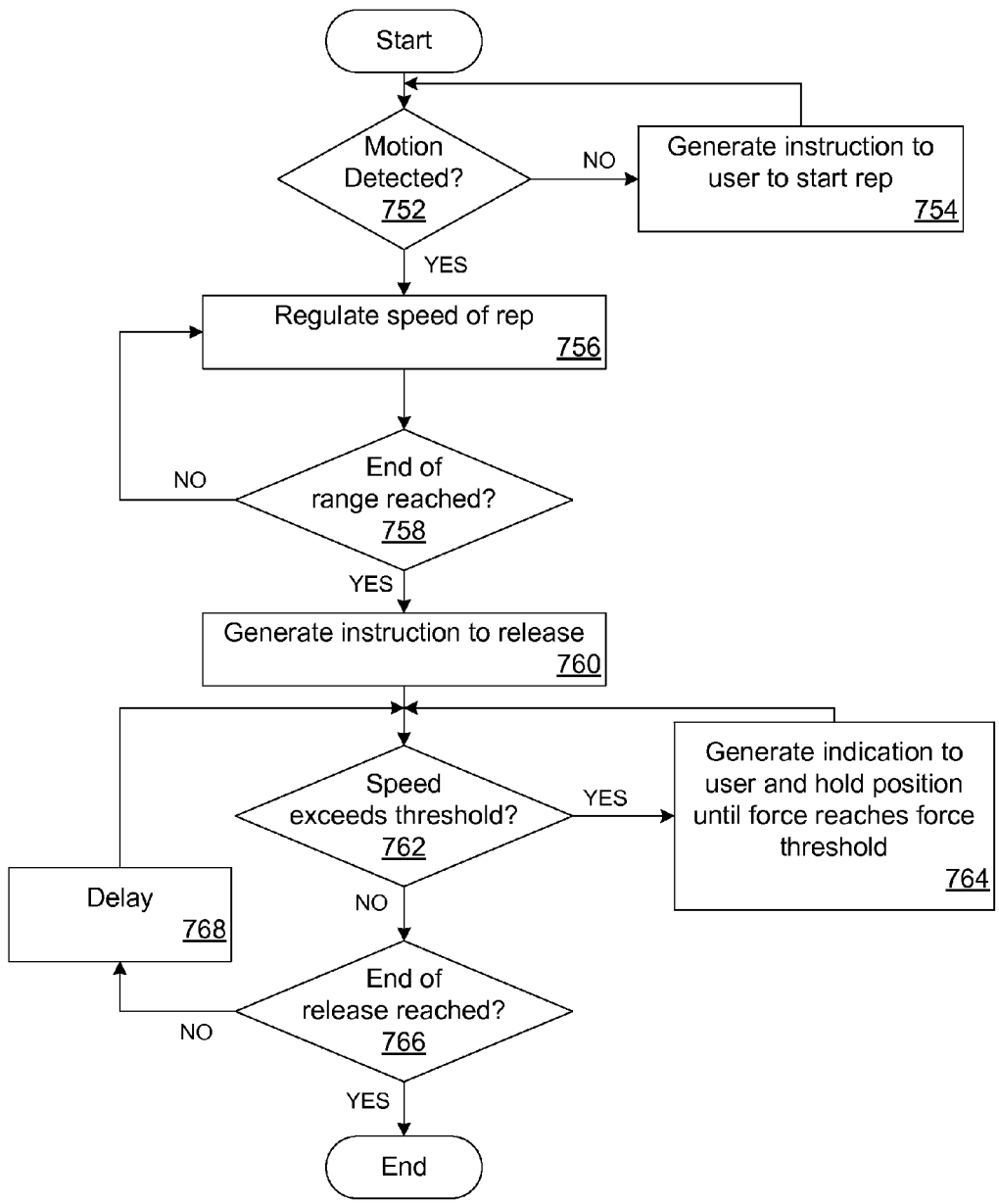
FIG. 7B is a flow diagram illustrating a method for updating an exercise program according to an implementation of the disclosure.
Figure 7C:
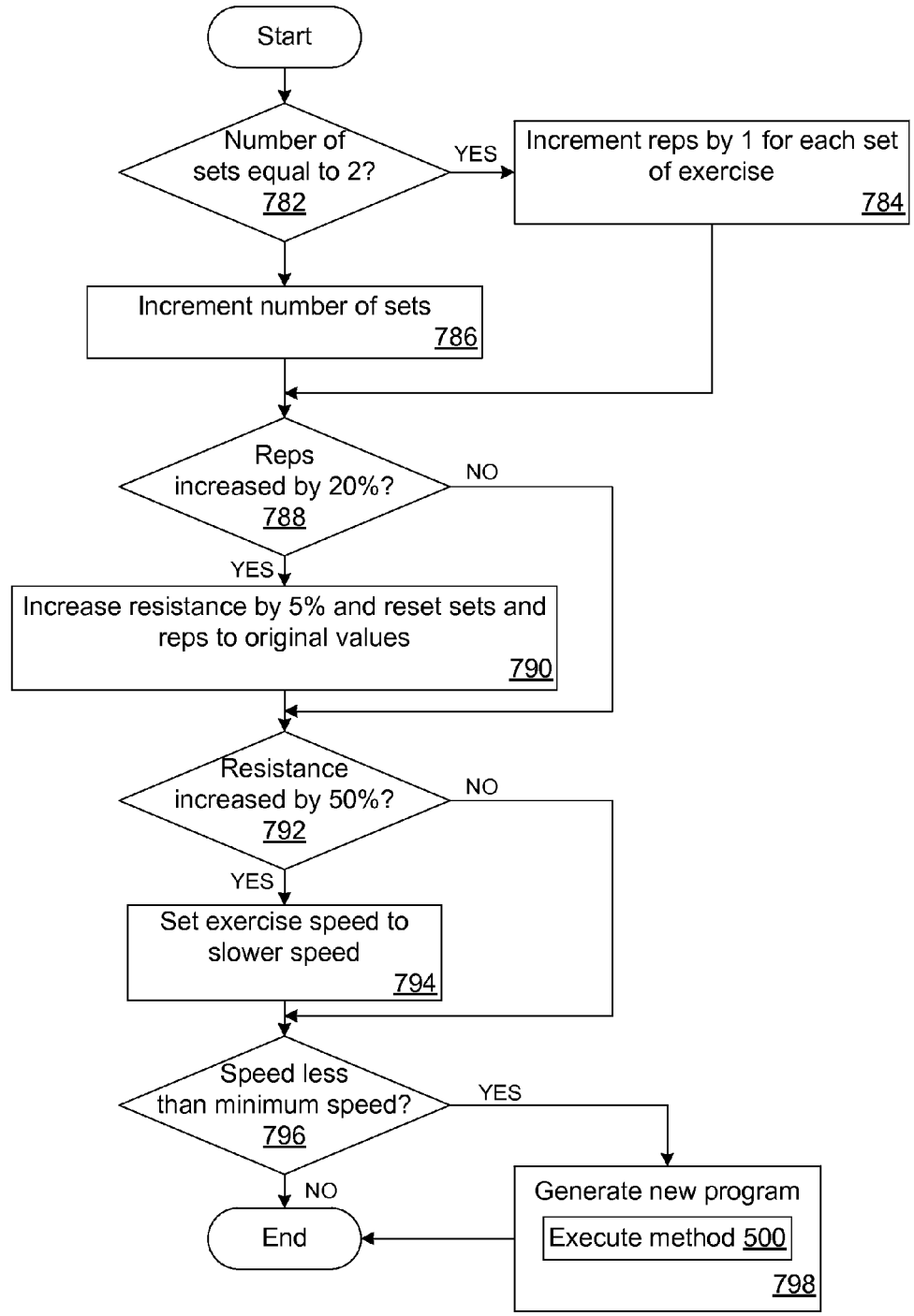
FIG. 7C is a flow diagram illustrating for enforcing a repetition according to an implementation of the disclosure.

Reference is now made to FIGS. 7A-7C are flow diagrams illustrating, respectively, the method 700 for executing an exercise program according to an implementation of the disclosure, a method 750 for updating an exercise program according to an implementation of the disclosure, and a method 780 for enforcing a repetition according to an implementation of the disclosure. The methods 700, 750, and 780 may each be performed by processing logic that includes hardware (e.g., circuitry, dedicated logic, programmable logic, microcode, etc.), software (e.g., instructions run on a processing device to perform hardware simulation), or a combination thereof. In some implementations, the methods 700, 750, and 780 may each be performed by the program management component 300, which may be implemented by one or more of the client devices 110A-110Z, the exercise server 120, one or more of the exercise devices 130A-130Z, or combinations thereof. In some implementations, the methods 700, 750, and 780 may each be performed at least partially by a user interface of a client device (e.g., any of user interfaces 112A-112Z of client devices 110A-110Z, respectively) as described with respect to in FIG. 1.

Referring to FIG. 7A, the method 700 is initiated at block 702 when exercise program data and exercise history data is retrieved (e.g., from the data store 140).

At block 704, a program timer is started. In one implementation, the program timer may be used to keep track of how long it takes a user to perform the exercise program. At the end of the method 700, the program timer may stop, and a total length of time measured by the program timer may be stored with exercise history data.

At block 706, an exercise set is selected. In one implementation, the exercise set may be selected based on schedule data. For example, if a particular exercise (e.g., standing curls) is scheduled to be performed at or near (e.g., within one to two hours) the current time, then standing curls will be selected as the exercise set to be performed. In one implementation, the exercise set may be selected in response to determining that the exercise is the next scheduled exercise to be performed (e.g., based on exercise history data). In one implementation, a user may select (e.g., using one of client devices 110A-110Z) the exercise set to perform.

At block 708, a resistance and speed is set for the selected exercise. For example, the resistance and speed may be identified within set table data (e.g., stored in the data store 140). In one implementation, the resistance and speed may be transmitted from a client device (e.g., one of client devices 110A-110Z) to one or more exercise devices (e.g., one or more of exercise devices 130A-130Z).

At block 710, instructions for performing the selected exercise may be generated (e.g., generated for display by one of client devices 110A-110Z). At block 712, a repetition of the exercise is enforced. In one implementation, block 710 is performed by the exercise device interface module 304. In one implementation, block 710 may further execute the method 750, which is described below with respect to FIG. 7B.

Referring to FIG. 7B, the method 750 begins at block 752 where a determination is made as to whether motion has occurred within an exercise device of the user. For example, a client device (e.g., one of client devices 110A-110Z) may receive an indication from one or more exercise devices (e.g., one of exercise devices 130A-130Z) as to whether or not the user has caused a respective handle of the one or more exercise devices to move beyond a pre-defined threshold (e.g., the user has applied a force to the handle displacing it by half of an inch). If no motion is detected, then the method 750 proceeds to block 754 where the user is instructed (e.g., by generating a visual or audio instruction) to perform the exercise. If motion is detected, then the method 750 proceeds to block 756 where a repetition speed is regulated. In one implementation, the repetition speed may be regulated such that the repetition speed is approximately (e.g., within 10-20%) of a target repetition speed of the exercise, as defined in the set table data. In one implementation, the repetition speed is regulated by the client device and/or a motor control unit of the exercise device. The client device may utilize feedback from the exercise device to ensure that the repetition speed is approximately equal to the target repetition speed by, for example, causing an increase in resistance if the user is displacing the handle of the exercise device faster than the target repetition speed. In one implementation, the repetition speed is regulated by generating (as a visual display and/or as an audio cue), with the client device, a counter that counts up to the total time for the repetition. For example, if the user is to displace the handle of the exercise device from a first position to a second position (e.g., fully relaxed to fully flexed) over a time duration (e.g., 8 seconds), the client device may generate a counter that counts up to the time duration (e.g., a count of 1, 2, 3, etc. up to 8 seconds).

At block 758, a determination is made as to whether an end of a range of the repetition has been reached. In one implementation, range may correspond to 90% of the maximum range of motion. In other implementations, other ratios of the maximum range may be used. If the end of the range has been reached, then the method 750 proceeds to block 760 where the user is instructed to begin releasing. In one implementation, a delay (e.g., 1 second) may occur between determining that the end of the range has been reached and instructing the user to begin releasing. If the end of the range has not been reached, then the method 750 proceeds back to block 756.

At block 762, a determination is made as to whether the repetition speed has exceeded a threshold repetition speed. In one implementation, the threshold speed may be a percentage of a target repetition speed (e.g., 10%, 20%, 30%, etc. of the target speed). If the threshold speed has been exceeded, then the method 750 proceeds to block 764 where an indication to the user is generated, and a position of a handle of the exercise device is held until a force threshold is reached. In one implementation, the position of the handle is held (e.g., maintained by the motor) until a force applied by the user is above a threshold value for maintaining a repetition speed within a target range set by the threshold repetition speed. If the threshold repetition speed was not exceeded, then the method 750 proceeds to block 766.

At block 766, if it is determined that an end of release has been reached (e.g., the user is at a fully relaxed position), then the method 750 ends. Otherwise, the method 750 proceeds to block 768 where a delay occurs before returning to block 762.

In some implementations, the exercise devices may prevent injury to the user by decreasing resistance or decreasing tension of the tension lines if, for example, the user exceeds a predetermined degree of flexation (e.g., a predetermined degree of knee flexation during a dead lift exercise). For example, for a given exercise and based on a height, body type, weight, etc. of the user, limits may be set for the exercise device and enforced by the exercise device in response to determining that a displacement of the handle has exceeded a range of the limits. In one implementation, the limits may be enforced by causing a motor of an exercise device to lock. In one implementation, the user may be warned by a client device (e.g., a visual or audio warning) that he/she has exceeded the limit.

Referring once again to FIG. 7A, after executing the method 750, the method 700 proceeds to block 714 where a determination is made as to whether the exercise set is complete. If the exercise set is not complete, then the method 700 proceeds back to block 712 where another repetition is enforced. If the exercise set is complete, then the method 700 proceeds to block 716, where a determination is made as to whether the exercise program is complete. If the exercise program is not complete, then the method 700 proceeds to block 718 where a rest time duration occurs. In one implementation, the rest time duration may have been previously defined and stored in the set table data. After the rest period, the method 700 proceeds to block 706 where another exercise set is selected. In one implementation, the newly selected exercise set may correspond to a next set of the current exercise. In one implementation, the newly selected exercise set may correspond to a set of a different exercise.

If, at block 716, it is determined that the exercise program has been completed, then the method 700 proceeds to block 720 where exercise progress is saved (e.g., stored as exercise history data 324A) and the exercise program is updated. In one implementation, block 720 is performed by the program generation module 306. In one implementation, block 710 may further execute the method 780, which is described below with respect to FIG. 7C. In one implementation, the method 780 may be executed for each exercise performed in the scheduled exercise program. In one implementation, the method 780 may be executed in response to determining that the user has successfully completed the scheduled exercise program. In one implementation, the method 780 may not be executed in response to determining that the user has failed to complete the scheduled exercise program. In one implementation, it may be determined that the user has failed to complete the scheduled exercise program in response to determining that the user was unable to complete all sets and all repetitions during execution of the exercise program (e.g., within a pre-determined workout session time duration). In one implementation, it may be determined that the user has failed to complete the scheduled exercise program in response to determining that the user exceeded a repetition speed and/or range threshold more than a predetermined number of times during execution of the exercise program.

Referring to FIG. 7C, the method 780 begins at block 782 where a determination is made as to whether a number of sets of a particular exercise is equal to a threshold number of sets. In one implementation, the threshold number of sets may be 2. In other implementations, the threshold number of sets may be different (e.g., 3, 4, etc.). If the number of sets is equal to the threshold number of sets, then the method 780 proceeds to block 784 where a number of repetitions for each of the sets of the particular exercise is incremented. In one implementation, the number of repetitions is incremented by 1. In other implementations, the number of repetitions is incremented by a different number (e.g., 2, 3, etc.). The method 780 then proceeds to block 788. If the number of sets is not equal to the threshold number of sets, then the method 780 proceeds to block 786 where the number of sets for the particular exercise is incremented. In one implementation, the number of sets is incremented by 1. In other implementations, the number of sets is incremented by a different number (e.g., 2, 3, etc.).

At block 788, a determination is made as to whether the total number of repetitions per set for the particular exercise has increased by a threshold number of repetitions compared to an initial number of repetitions. In one implementation, the threshold number of repetitions corresponds to a 20% increase in the initial number of repetitions. In other implementations, the threshold number of repetitions corresponds to a different increase in the initial number of repetitions (e.g., 10%, 30%, etc.). In one implementation, the initial number of repetitions may be determined from exercise history data, and the initial number of repetitions may correspond to the repetitions determined when the set table data was first generated for the user.

If, at block 788, it is determined that the total number of repetitions is greater than or equal to the threshold number of repetitions, the method 780 proceeds to block 790. Otherwise, the method 780 proceeds to block 792.

At block 790, a resistance of the particular exercise is increased. In one implementation, the resistance is increased by a fraction of its current value. In one implementation, the resistance is increased by a fraction of its initial value. In one implementation, the fraction is 5%. In other implementations, the fraction is a different number (e.g., 10%, 15%, 20%, etc.). In one implementation, the number of sets and/or the number of repetitions per set are reset to their initial values (e.g., their values when the set table data was generated).

At block 792, a determination is made as to whether the resistance for the particular exercise has increased by a threshold resistance compared to an initial resistance. In one implementation, the threshold resistance corresponds to a 50% increase in the initial resistance. In other implementations, the threshold resistance corresponds to a different increase in the initial resistance (e.g., 10%, 20%, 30%, 40%, 60%, etc.). In one implementation, the initial resistance may be determined from exercise history data, and the initial resistance may correspond to the resistance determined when the set table data was first generated for the user.

If, at block 792, it is determined that the resistance is greater than or equal to the threshold resistance, the method 780 proceeds to block 794. Otherwise, the method 780 proceeds to block 796.

At block 794, a repetition speed of the particular exercise is decreased. In one implementation, the repetition speed may be decreased by a fixed amount. In one implementation, the repetition speed may be set to a pre-defined lower repetition speed. In one implementation, the repetition speed may be divided by a factor (e.g., a factor of 2, such that the initial repetition speed of 1 rep per 4 seconds is decreased to 1 rep per 8 seconds).

At block 796, a determination is made as to whether the repetition speed of the particular exercise is less than or equal to a minimum repetition speed for the particular exercise. In one implementation, the minimum repetition speed is 1 rep per 16 seconds. In other implementations, the minimum repetition speed may is different (e.g., 1 rep per 14 seconds, 1 rep per 15 seconds, 1 rep per 17 seconds, etc.).

If, at block 796, it is determined that the repetition speed is less than the minimum repetition speed (or less than or equal to in some implementations), then the method 780 proceeds to block 798. Otherwise, the method 780 ends. In one implementation, at block 798, a new exercise program is generated for the user (e.g., by executing the method 500). This may occur when the user has improved his/her performance over the course of several scheduled workouts, and the user's one-rep maxima for each exercise has increased as a result. A new exercise program may be generated based at least partially on new one-rep maxima obtained for each exercise to be included in the new exercise program.

Referring once again to FIG. 7A, after executing the method 780, the method 700 ends.

Referring once again to FIG. 4, after executing the method 700, the method 400 ends. The method 400 may be repeated continuously. In some implementations, less than all of the blocks of the method 400 may be performed.

For simplicity of explanation, the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events. Additionally, it should be appreciated that the methods disclosed in this specification are capable of being stored on an article of manufacture, such as a computer-readable device or storage medium, to facilitate transporting and transferring such methods to computing devices. Accordingly, the term "article of manufacture", as used herein, is intended to include a computer program accessible from any computer-readable device or storage medium.

Figure 8:
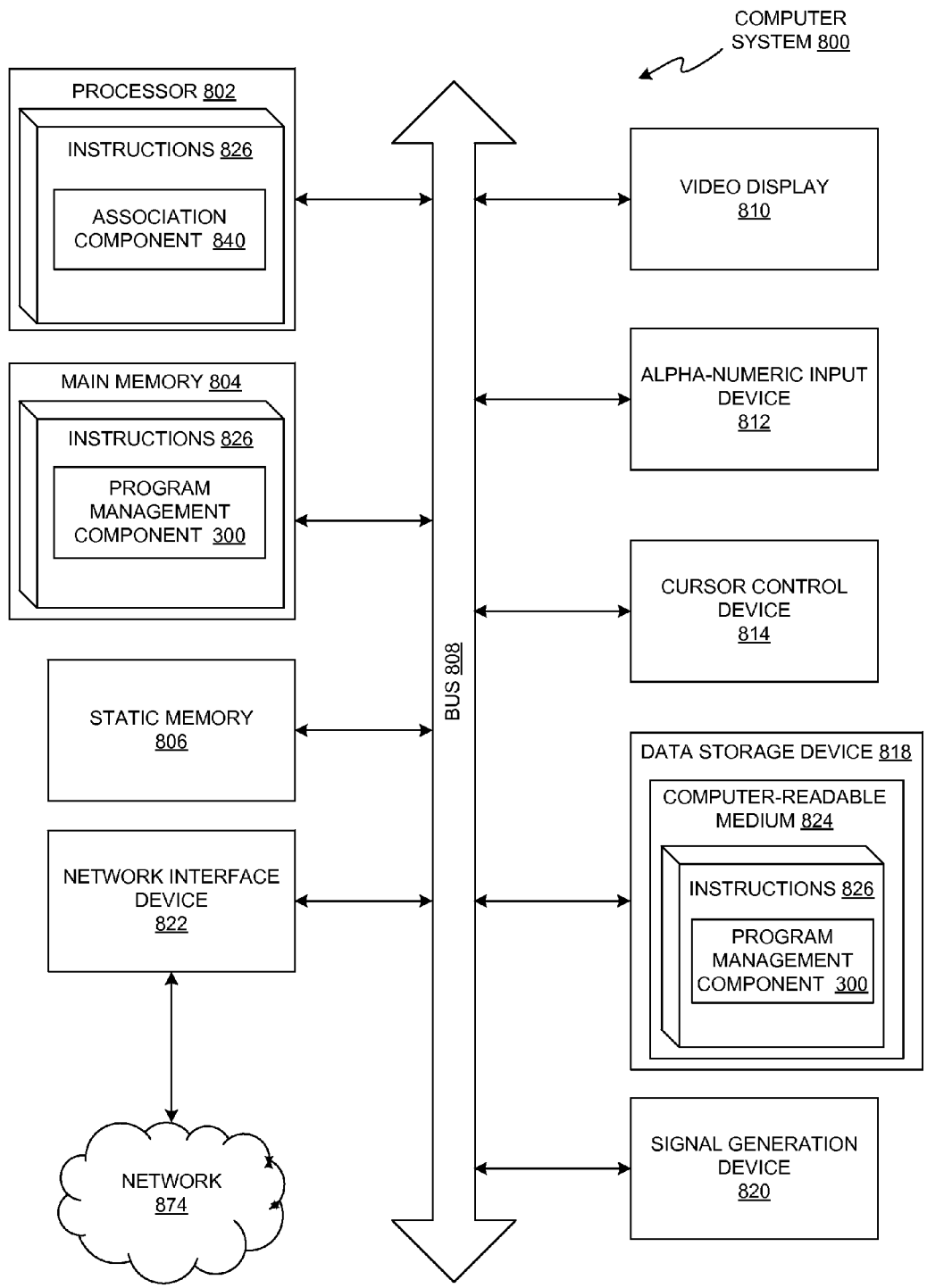
FIG. 8 is a block diagram illustrating an exemplary computer system for use in accordance an implementation of the disclosure.

FIG. 8 illustrates a diagrammatic representation of a machine in the exemplary form of a computer system 800 within which a set of instructions, for causing the machine to perform any one or more of the methodologies discussed herein, may be executed. In alternative implementations, the machine may be connected (e.g., networked) to other machines in a LAN, an intranet, an extranet, or the Internet. The machine may operate in the capacity of a server or a client machine in client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Some or all of the components of the computer system 800 may be utilized by or illustrative of any of the client devices 110A-110Z, the exercise server 120, any of the exercise devices 130A-130Z (e.g., any of motor control units 132A-132Z), and the data store 140.

The exemplary computer system 800 includes a processing device (processor) 802, a main memory 804 (e.g., read-only memory (ROM), flash memory, dynamic random access memory (DRAM) such as synchronous DRAM (SDRAM) or Rambus DRAM (RDRAM), etc.), a static memory 806 (e.g., flash memory, static random access memory (SRAM), etc.), and a data storage device 818, which communicate with each other via a bus 808.

Processor 802 represents one or more general-purpose processing devices such as a microprocessor, central processing unit, or the like. More particularly, the processor 802 may be a CISC microprocessor, a RISC microprocessor, a VLIW microprocessor, or a processor implementing other instruction sets or processors implementing a combination of instruction sets. The processor 802 may also be one or more special-purpose processing devices such as an ASIC, an FPGA, a DSP, a network processor, or the like. The processor 802 is configured to execute instructions 826 for performing the operations and steps discussed herein.

The computer system 800 may further include a network interface device 822. The computer system 800 also may include a video display unit 810 (e.g., a liquid crystal display (LCD), a cathode ray tube (CRT), or a touch screen), an alphanumeric input device 812 (e.g., a keyboard), a cursor control device 814 (e.g., a mouse), and a signal generation device 820 (e.g., a speaker). In some implementations, the signal generation device 820 may include a vibrational actuator (e.g., for providing haptic feedback).

The data storage device 818 may include a computer-readable storage medium 824 on which is stored one or more sets of instructions 826 (e.g., software) embodying any one or more of the methodologies or functions described herein. The instructions 826 may also reside, completely or at least partially, within the main memory 804 and/or within the processor 802 during execution thereof by the computer system 800, the main memory 804 and the processor 802 also constituting computer-readable storage media. The instructions 826 may further be transmitted or received over a network 874 (e.g., the network 150) via the network interface device 822.

In one implementation, the instructions 826 include instructions for one or more program management components 300, which may correspond to the identically-named counterpart described with respect to FIGS. 1 and 3. While the computer-readable storage medium 824 is shown in an exemplary implementation to be a single medium, the terms "computer-readable storage medium" or "machine-readable storage medium" should be taken to include a single medium or multiple media (e.g., a centralized or distributed database, and/or associated caches and servers) that store the one or more sets of instructions. The terms "computer-readable storage medium" or "machine-readable storage medium" shall also be taken to include any transitory or non-transitory medium that is capable of storing, encoding or carrying a set of instructions for execution by the machine and that cause the machine to perform any one or more of the methodologies of the present disclosure. The terms "computer-readable storage medium" or "machine-readable storage medium" shall accordingly be taken to include, but not be limited to, solid-state memories, optical media, and magnetic media.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Some portions of the detailed description may have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is herein, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "sending", "receiving", "transmitting", "forwarding", "caching", "causing", "providing", "generating", "adding", "subtracting", "removing", "analyzing", "determining", "enabling", "identifying", "modifying" or the like, refer to the actions and processes of a computer system, or similar electronic computing device, that manipulate and transform data represented as physical (e.g., electronic) quantities within the computer system's registers and memories into other data similarly represented as physical quantities within the computer system memories or registers or other such information storage, transmission or display devices.

The disclosure also relates to an apparatus, device, or system for performing the operations herein. This apparatus, device, or system may be specially constructed for the required purposes, or it may include a general purpose computer selectively activated or reconfigured by a computer program stored in the computer. Such a computer program may be stored in a computer- or machine-readable storage medium, such as, but not limited to, any type of disk including floppy disks, optical disks, compact disk read-only memories (CD-ROMs), and magnetic-optical disks, read-only memories (ROMs), random access memories (RAMs), EPROMs, EEPROMs, magnetic or optical cards, or any type of media suitable for storing electronic instructions.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an implementation" or "one implementation" means that a particular feature, structure, or characteristic described in connection with the implementation is included in at least one implementation. Thus, the appearances of the phrase "an implementation" or "one implementation" in various places throughout this specification are not necessarily all referring to the same implementation. Moreover, it is noted that the "A-Z" notation used in reference to certain elements of the drawings is not intended to be limiting to a particular number of elements. Thus, "A-Z" is to be construed as having one or more of the element present in a particular implementation.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A method of using an exercise device, the method comprising:
   identifying, by a processing device, one or more parameters of a user;
   identifying, by the processing device, force data associated with the user, the force data corresponding to a force measured while the user performed an exercise;
   generating, by the processing device, an exercise program to be executed using the exercise device; and
   computing, by the processing device, a resistance to be applied by the exercise device during execution of the exercise program, wherein computing the resistance comprises multiplying the force by a fractional multiplier selected based on the one or more parameters of the user.

2. The method of claim 1, wherein the force corresponds to a one-rep maximum of the user for the exercise.

3. The method of claim 1. further comprising:
   generating, by the processing device, an indication to the user to perform the exercise; and
   causing the exercise device to apply the resistance as the user performs the exercise.

4. The method of claim 1, wherein identifying the force data comprises:
   generating, by the processing device, an indication to the user to perform the exercise;
   receiving the force data from the exercise device as the user applies a force to a handle of the exercise device, wherein the exercise device captures the force data over a time duration, and wherein the exercise device maintains a relative location of the handle as the user applies the force to the handle during the time duration;
   computing one-rep maximum data based on the force data: and
   storing, in a memory communicatively coupled to the processing device, the one-rep maximum data for the exercise.

5. The method of claim 1, wherein generating the exercise program comprises: generating set table data comprising one or more of a number of sets to be performed for the exercise, a number of repetitions to be performed for a respective set the exercise, an initial resistance for the exercise, or a repetition speed for the exercise; and storing the set table data in a memory communicatively coupled to the processing device.

6. The method of claim 1. further comprising:
   determining, for the exercise, a time duration, wherein the time duration corresponds to a total workout time to perform a respective number of sets and a respective number of repetitions for the exercise; and
   generating schedule data based on at least one of the time duration of the exercise, a user- preferred time, or an exercise goal.

7. The method of claim 1, wherein identifying the one or more parameters comprise receiving the one or more parameters as user inputs at a client device.

8. The method of claim 1, wherein the one or more parameters comprise an exercise goal of the user, and wherein the fractional multiplier is selected based on the exercise goal of the user.

9. The method of claim 1, wherein the exercise device comprises the processing device.

10. The method of claim 1, wherein client device comprises the processing device, and wherein the client device is communicatively coupled to the exercise device.

* * * * *